(12) United States Patent
Rashidi et al.

(10) Patent No.: US 11,424,028 B2
(45) Date of Patent: Aug. 23, 2022

(54) METHOD AND APPARATUS FOR PERVASIVE PATIENT MONITORING

(71) Applicant: University of Florida Research Foundation, Incorporated, Gainesville, FL (US)

(72) Inventors: Parisa Rashidi, Gainesville, FL (US); Azra Bihorac, Gainesville, FL (US); Patrick J. Tighe, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 540 days.

(21) Appl. No.: 16/388,351

(22) Filed: Apr. 18, 2019

(65) Prior Publication Data

US 2019/0326013 A1    Oct. 24, 2019

Related U.S. Application Data

(60) Provisional application No. 62/659,948, filed on Apr. 19, 2018.

(51) Int. Cl.
*G16H 40/63* (2018.01)
*G06K 9/62* (2022.01)
(Continued)

(52) U.S. Cl.
CPC .......... *G16H 40/63* (2018.01); *A61B 5/0077* (2013.01); *A61B 5/1114* (2013.01);
(Continued)

(58) Field of Classification Search
CPC ........ G16H 40/63; G16H 50/20; G16H 10/60; G16H 30/40; G06K 9/00302;
(Continued)

(56) References Cited

U.S. PATENT DOCUMENTS

| 7,420,472 B2 | 9/2008 | Tran |
| 2007/0085690 A1* | 4/2007 | Tran ...................... G08B 21/04 340/573.1 |

(Continued)

FOREIGN PATENT DOCUMENTS

| CN | 10735 8180 A | 11/2017 |
| CN | 107895160 A | 4/2018 |
| WO | WO-2018/067684 A1 | 4/2018 |

OTHER PUBLICATIONS

Barr, Juliana et al. *Clinical Practice Guidelients for he Management of Pain, Agitation, and Delirium in Adult Patients in the Intensive Care Unit*, Critical Care Medicine, vol. 41, No. 1, pp. 263-306, Jan. 2013.

(Continued)

*Primary Examiner* — Ryan W Sherwin
(74) *Attorney, Agent, or Firm* — Alston & Bird LLP

(57) ABSTRACT

A patient monitoring system comprises a plurality of sensors and an analysis computing entity. The sensors comprise a visual sensor and a wearable sensor. The visual sensor is configured to capture images of a patient and provide the images of the patient such that the analysis computing entity receives the images. The wearable sensor is configured to capture wearable data. The wearable data comprises (a) biometric data of the patient and/or (b) movement data of the patient. The wearable sensor is configured to provide the wearable data such that the analysis computing entity receives the wearable data. The analysis computing entity is configured to receive the images of the patient and the wearable data, analyze at least one of the images of the patient and the wearable data to determine objective patient data, and update a patient record based on the objective patient data.

18 Claims, 11 Drawing Sheets

(51) Int. Cl.

| | |
|---|---|
| A61B 5/00 | (2006.01) |
| A61B 5/11 | (2006.01) |
| A61B 5/16 | (2006.01) |
| G16H 50/20 | (2018.01) |
| G16H 10/60 | (2018.01) |
| G06V 40/20 | (2022.01) |
| G06V 40/16 | (2022.01) |

(52) U.S. Cl.
CPC ............ *A61B 5/1116* (2013.01); *A61B 5/165* (2013.01); *A61B 5/6801* (2013.01); *A61B 5/7267* (2013.01); *A61B 5/7282* (2013.01); *A61B 5/746* (2013.01); *G06K 9/6267* (2013.01); *G06V 40/172* (2022.01); *G06V 40/174* (2022.01); *G06V 40/23* (2022.01); *G16H 10/60* (2018.01); *G16H 50/20* (2018.01); *A61B 2560/0242* (2013.01); *A61B 2562/0219* (2013.01); *A61B 2576/02* (2013.01)

(58) Field of Classification Search
CPC ........... G06K 9/00342; G06K 9/00288; G06K 9/6267; G06K 9/00228; G06K 9/00771; A61B 5/0077; A61B 5/6801; A61B 5/1114; A61B 5/1116; A61B 5/7267; A61B 5/165; A61B 5/7282; A61B 5/746; A61B 2562/0219; A61B 2576/02; A61B 2560/0242; A61B 5/0205; A61B 5/11; A61B 5/002

See application file for complete search history.

(56) References Cited

U.S. PATENT DOCUMENTS

| | | | |
|---|---|---|---|
| 2008/0077001 A1 | 3/2008 | Ruscio et al. | |
| 2013/0085771 A1* | 4/2013 | Ghanbari | G16H 20/10 705/2 |
| 2013/0127620 A1* | 5/2013 | Siebers | A61B 5/1113 340/573.1 |
| 2014/0121927 A1* | 5/2014 | Hanita | B60T 7/14 701/70 |
| 2015/0109442 A1 | 4/2015 | Derenne et al. | |
| 2018/0032694 A1* | 2/2018 | Van Den Heuvel | A61G 7/0507 |
| 2019/0286892 A1* | 9/2019 | Li | G06K 9/00362 |

OTHER PUBLICATIONS

Thrush, Aaron et al. *The Clinical Utility of the Functional Status Score for the Intensive Care Unit (FSS-ICU) at a Long-Term Acute Care Hospital: A Prospective Cohort Study*, Physical Therapy, vol. 92, No. 12, pp. 1536-1545, Dec. 2012.
Brown, Harvey et al. *Continuous Monitoring in an Inpatient Medical-Surgical Unit: A Controled Clinical Trial*, The American Journal of Medicine, vol. 127, No. 3, pp. 226-232, Mar. 2014.
Vincent, Jean-Louis et al. *Paradigm Shifts in Critical Care Medicine: The Progress We Have Made*, Critical Care, vol. 19, No. Suppl 3, pp. 1-6, Dec. 2015.
Ely, E. Wesley et al. *Evaluation of Delirium in Critically Ill Patients: Validation of the Confusion Assessment Method for the Intensive Care Unit (CAM-ICU)*, Critical Care Medicine, vol. 29, No. 7, pp. 1370-1379, (2001).
Meagher, D. et al. *Development of an Abbreviated Version of the Delirium Motor Subtyping Scale (DMSS-4)*, International Psychogeriatrics, vol. 26, No. 4, pp. 693-702, (2014).
Zhang, Kaipeng et al. *Joint Face Detection and Alignment Using Multitask Cascaded Convolutional Networks*, IEEE Signal Processing Letters, vol. 23, No. 10, pp. 1499-1503, (2016).
Schroff, Florian et al. *FaceNet: A Unified Embedding for Face Recognition and Clustering*, in 2015 IEEE Conference on Computer Vision and Pattern Recognition (CVPR), pp. 815-823, (2015).
Szegedy, Christian et al. *Inception-V4, Inception-Resnet and the Impact of Residual Connections on Learning*, in Thirty-First AAAI Conference On Artificial Intelligence, pp. 4278-4284, Feb. 12, 2017. arXiv:1602.07261v2 [cs.CV] Aug. 23, 2016.
Cao, Zhe et al. *Realtime Multi-Person 2D Pose Estimation Using Part Affinity Fields*, Computing Research Repository, (9 pages), 2016. arXiv:1611.08050v2 [cs.CV] Apr. 14, 2017.
Amos, Brandon et al. *OpenFace: A General-Purpose Face Recognition Library With Mobile Applications*, in "CMU-CS-16-118," CMU School of Computer Science, (20 pages), Jun. 2016.
Buckenmaier III, Chester C. et al. *Preliminary Validation of the Defense and Veterans Pain Rating Scale (DVPRS) in a Military Population*, Pain Medicine, vol. 14, No. 1, pp. 110-123, (2013).
Godfrey, Alan et al. *Motion Analysis in Delirium: A Discrete Approach in Determining Physical Activity for the Purpose of Delirium Motoric Subtyping*, Medical Engineering & Physics, vol. 32, No. 2, pp. 101-110, Mar. 2010.
Meagher, David J. et al., *Motor Symptoms in 100 Patients With Delirium Versus Control Subjects: Comparison of Subtyping Methods*, Psychosomatics, vol. 49, No. 4, pp. 300-308, Jul.-Aug. 2008.
Cooke, Alexandr B. et al. *The Impact of Accelerometer Wear Location on the Relationship Between Step Counts and Arterial Stiffness in Adults Treated for Hypertension and Diabetes*, Journal of Science and Medicine in Sport, vol. 21, pp. 398-403, (2018).
Rosenberger, Mary E. et al. *Estimating Activity and Sedentary Behavior From an Accelerometer on the Hip or Wrist*, Medicine and Science in Sports & Exercise, vol. 45, No. 5, pp. 964-975, (2013).
Montoye, Alexander H.K. et al. *Validation and Comparison of Accelerometers Worn on the Hip, Thigh, and Wrists for Measuring Physical Activity and Sedentaty Behavior*, AIMS Public Health, vol. 3, No. 2, pp. 298- 312, May 20, 2016. DOI: 10.3934/publichealth.2016.2.298.
Sasaki, Jeffer E. et al. *Validation and Comparison of Actigraph Activity Monitors*, Journal of Science and Medicine in Sport, vol. 14, No. 5, pp. 411-416, (2011).
Lucey, Patrick et al. *Automatically Detecting Pain in Video Through Facial Action Units*, IEEE Transactions on Systems, Man, and Cybernetics, Part B (Cybernetics), vol. 41, No. 3, pp. 664-674, Jun. 2011.
Tipping, Claire J. et al. *The ICU Mobility Scale Has Construct and Predictive Validity and is Responsive. A Multicenter Observational Study*, Annals of the American Thoracic Society, vol. 13, No. 6, pp. 887-893, (2016).
Bourdev, Lubomir et al. *Poselets: Body Part Detectors Trained Using 3D Human Pose Annotations*, in Computer Vision, in 2009 IEEE 12th International Conference on Computer Vision, pp. 1365-1372, Sep. 27, 2009. IEEE.
Felzenszwalb, Pedro F. et al. *Object Detection with Discriminatively Trained Part-Based Models*, IEEE Transactions on Pattern Analysis and Machine Intelligence, vol. 32, No. 9, pp. 1627-1645, (2010).
Weinberger, Kilian Q. et al. *Distance Metric Learning for Large Margin Nearest Neighbor Classification*, Journal of Machine Learning Research, vol. 10, pp. 207-244, Feb. 2009.
Huang, Gary B. et al. *Labeled Faced in the Wild: A Database for Studying Face Recognition in Unconstrained Environments*, Technical Report 07-49, pp. 1-11, (2007), University of Massachusetts, Amherst, Massachusetts.
Felzenszwalb, Pedro F. et al. *Pictorial Structures for Object Recognition*, International Journal of Computer Vision, vol. 61, No. 1, pp. 55-79, (2005).
Papandreou, George et al., *Towards Accurate Multi-Person Pose Estimation in the Wild*, pp. 1-9, (2017). arXiv preprint arXiv:1701.01779v2 [cs.CV] Apr. 14, 2017.
Sun, Min et al. *Articulated Part-Based Model for Joint Object Detection and Pose Estimation*, in 2011 International Conference on Computer Vision, pp. 723-730, Nov. 6, 2011. IEEE.
Long, Jonathan et al. *Fully Convolutional Networks for Semantic Segmentation*, in Proceedings of the IEEE Conference on Computer Vision and Pattern Recognition, pp. 3431-3440, (2015).

(56) References Cited

OTHER PUBLICATIONS

Simonyan, Karen et al. *Very Deep Convolutional Networks for Large-Scale Image Recognition.* (14 pages), Published as a conference paper at ICLR 2015. arXiv preprint arXiv:1409.1556v6 [cs.CV] Apr. 10, 2015.

Pishchulin, Leonid et al. *Articulated People Detection and Pose Estimation: Reshaping the Future*, in 2012 IEEE Conference on Computer Vision and Pattern Recognition, pp. 3178-3185, (2012).

Troyanskaya, Olga et al., *Missing Value Estimation Methods for DNA Microarrays*, Bioinformatics, vol. 17, No. 6, pp. 520-525, Jun. 2001.

Yeung, Serena et al. *A Computer Vision System for Deep Learning-Based Detection of Patient Mobilization Activities in the ICU*, NPJ Digital Medicine, vol. 2, No. 1, pp. 1-5, (2019).

Ma, Andy J. et al. *Measuring Patient Mobility in the ICU Using a Novel Noninvasive Sensor*, Critical Care Medicine, vol. 45, No. 4, pp. 630-637, Apr. 2017.

Bin Mansour, Muhammad Naufal et al. *Patient Monitoring in ICU Under Unstructured Lighting Condition, 2010 IEEE Symposium on Industrial Electronics and Applications (ISIEA)*, Oct. 2010, pp. 608-611, Penang, Malaysia. DOI: 10.1109/ISIEA.2010.5679394.

Zhang, Li et al. *Intelligent Facial Emotion Recognition and Semantic Based Topic Detection for a Humanoid Robot*, Expert Systems With Applications, vol. 40, Issue 13, Oct. 1, 2013, pp. 5160-5168. DOI: 10.1016/j.eswa.2013.03.016.

Ma, Andy J. et al. *Measuring Patient Mobility in the ICU Using a Novel NonInvasive Sensor*, Critical Care Medicine, vol. 45, Issue 4, Apr. 1, 2017, pp. 630-636.

\* cited by examiner

METHOD AND APPARATUS FOR PERVASIVE PATIENT MONITORING

CROSS-REFERENCE TO RELATED APPLICATIONS

This application claims priority to and the benefit of U.S. Provisional Patent Application No. 62/659,948, filed Apr. 19, 2018, the contents of which are hereby incorporated by reference in their entirety.

STATEMENT REGARDING FEDERALLY SPONSORED RESEARCH OR DEVELOPMENT

This invention was made with government support under grant number 1750192 awarded by the National Science Foundation and under R21 EB027344 awarded by National Institute of Health/NIBIB. The government has certain rights in the invention.

BACKGROUND

Effective patient care relies at least partially on an accurate understanding of a plethora of both clinical, physiological, and sometimes psychological information regarding a patient. In many care environments, such as hospitals (e.g., Intensive Care Units), home-based care centers, and/or the like, patients are monitored through a number of existing sensors (e.g., blood pressure sensors, heart rate sensors, and/or the like) as well as through information gleaned from care provider (e.g., nurse, doctor, physician's assistant, and/or the like) interviews of the patient. For example, care-providers may question the patient about his/her mood, level of perceived pain, alertness, and/or the like. However, the combination of information sources about a patient's current clinical, physiological, and/or psychological state still do not provide an entirely complete and/or objective view of the patient's current state. Information gaps in this patient-specific information can easily grow during busy periods in care providers' schedules (resulting in shorter and/or fewer visits of the care provider to the patient). Thus, a need exists for objective patient monitoring systems and methods for automatically collecting and/or providing clinical and/or physiological information about specific patients.

BRIEF SUMMARY

To meet this need and others, example embodiments of the present invention provide methods, apparatus, systems, computing devices, computing entities, and/or the like for monitoring patient activity and/or environmental characteristics within a patient's room. In this regard, example embodiments utilize one or more wearable and/or patient mounted sensors (e.g., accelerometers), one or more environmental sensors (e.g., light sensors, sound sensors, and/or the like) and one or more visual sensors (e.g., cameras) in combination with a machine-learning analytics framework to collect, generate, and/or record patient data to ascertain the physiological state of a patient, such as whether the patient is delirious or non-delirious. Various embodiments may provide patient specific information/data to care providers such that a care regimen for a patient may be modified to provide a better patient experience and/or to better address the patient's medical and/or other needs, provide an alert to care providers when a patient intervention may be needed and/or effective, and/or the like.

According to a first aspect of the present invention, a patient monitoring system is provided. In an example embodiment, the patient monitoring system comprises a plurality of sensors. The plurality of sensors comprises at least one visual sensor and at least one wearable sensor. The at least one visual sensor is configured to capture images of a patient and provide the images of the patient such that an analysis computing entity receives the images of the patient. The at least one wearable sensor is configured to capture wearable data. The wearable data comprises at least one of (a) biometric data of the patient or (b) movement data of the patient. The at least one wearable sensor is configured to provide the wearable data such that the analysis computing entity receives the wearable data. The system further comprises an analysis computing entity. The analysis computing entity comprises a processor, a memory storing computer program code, and a communications interface. The memory and computer program code, with the processor, configured to cause the analysis computing entity to at least receive the images of the patient and the wearable data, analyze at least one of the images of the patient and the wearable data to determine objective patient data, and update a patient record based on the objective patient data.

According to another aspect of the present invention, a method for notifying a care provider about a condition of a patient is provided. In an example embodiment, the method comprises receiving, by an analysis computing entity, sensor data corresponding to a patient. The sensor data was captured by a plurality of sensors located in the proximity of the patient (e.g., within the patient's room, in an example embodiment). The sensor data comprises a sequence of images of the patient and wearable data captured by a wearable sensor worn by the patient. The method further comprises analyzing, by the analysis computing entity, at least one of (a) the sequence of images of the patient to determine at least one of (i) changes to head position of the patient or (ii) facial expressions of the patient or (b) the wearable data to determine patient movement data for the patient. The method further comprises, based on at least one of the (a) changes in head position of the patient or facial expressions of the patient or (b) wrist movement data for the patient, determining, by the analysis computing entity, whether a trigger event has occurred. In an example embodiment, when it is determined that a trigger event has occurred, generating and providing an alert indicating that the trigger event has occurred such that a user computing entity receives the alert, the user computing entity configured to provide a user-perceivable notification of the alert via a user interface thereof.

BRIEF DESCRIPTION OF THE SEVERAL VIEWS OF THE DRAWING(S)

Having thus described the invention in general terms, reference will now be made to the accompanying drawings, which are not necessarily drawn to scale.

Figure 5:
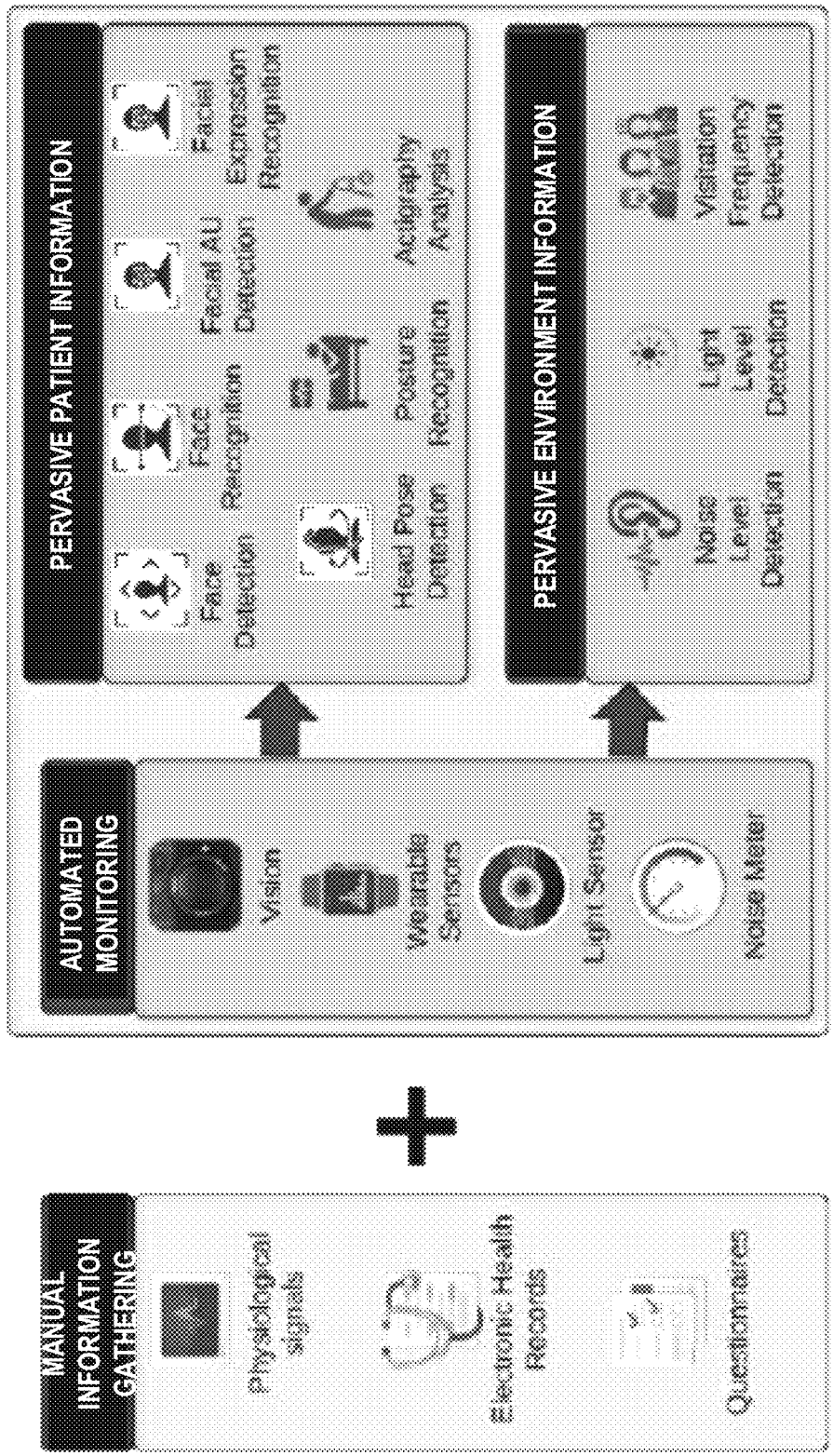

FIG. 5 provides a schematic diagram of the information/data captured and/or available to care providers via manual patient monitoring and automated patient monitoring according to an example embodiment.

Figure 6:
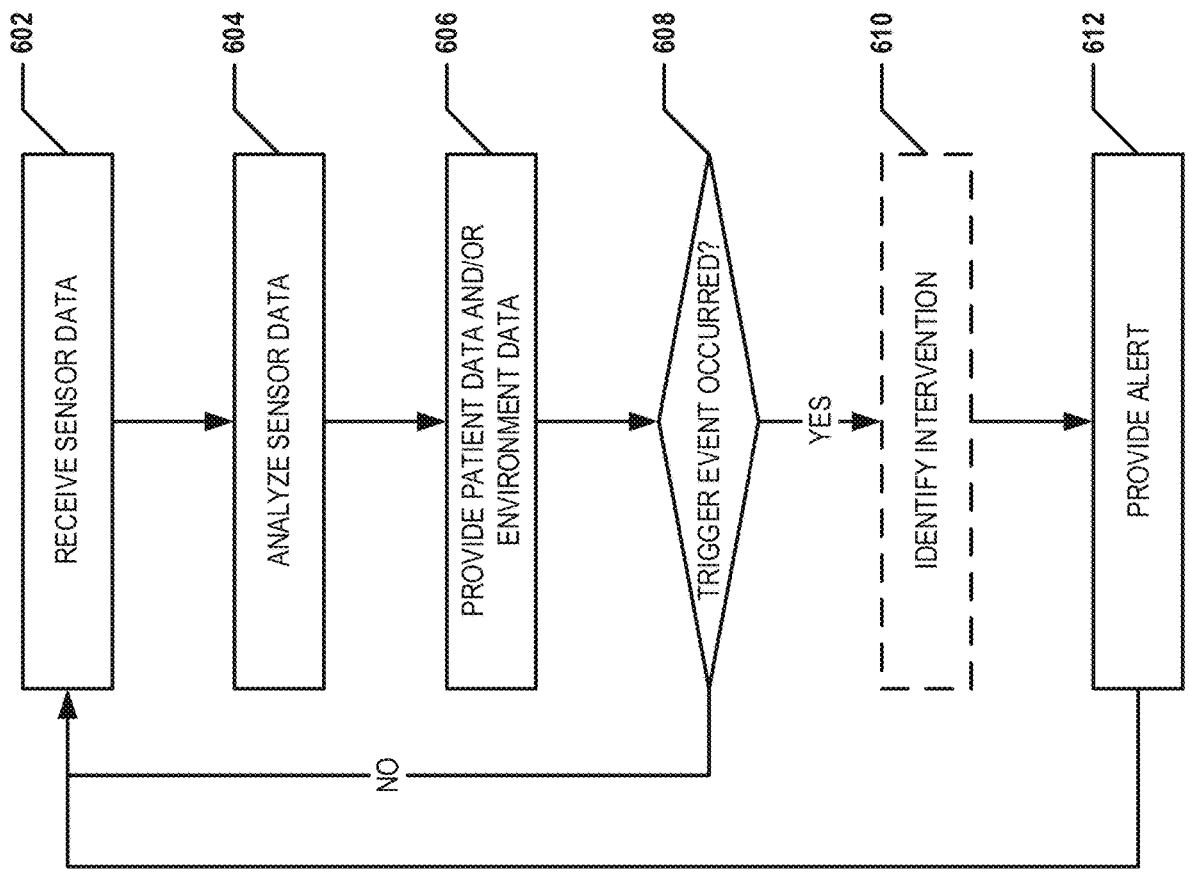

FIG. 6 provides a flowchart illustrating various processes, procedures, and/or operations performed, for example by an analysis computing entity, for providing patient information/data and/or providing an alert corresponding to a patient according to an example embodiment.

Figure 6A:
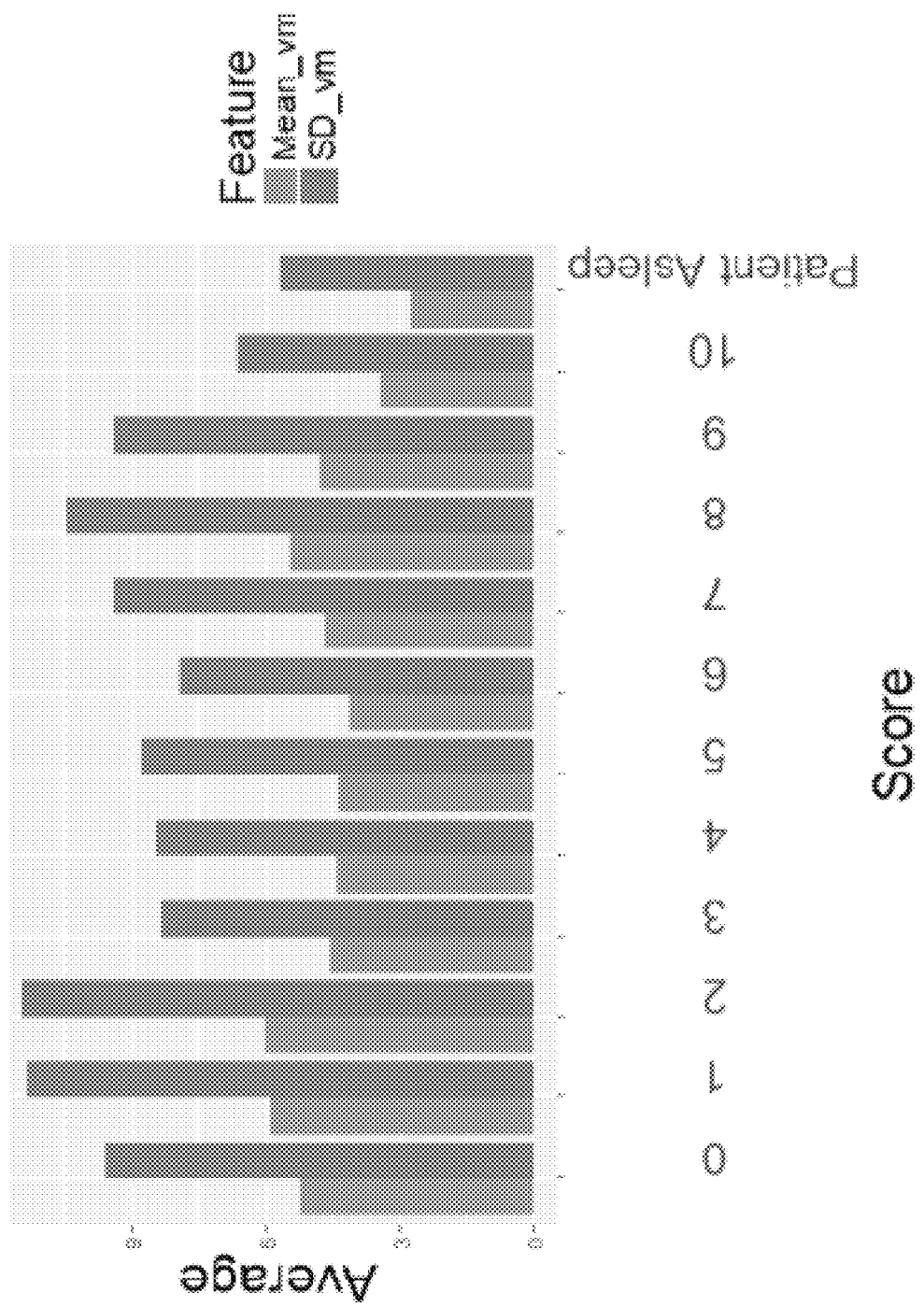

FIG. 6A provides a plot illustrating the observed distribution of mean and standard deviation of accelerometer vector magnitude with respect to nurse-assessed pain scores for a group of patients observed using a patient monitoring system in accordance with the present invention.

Figure 7:
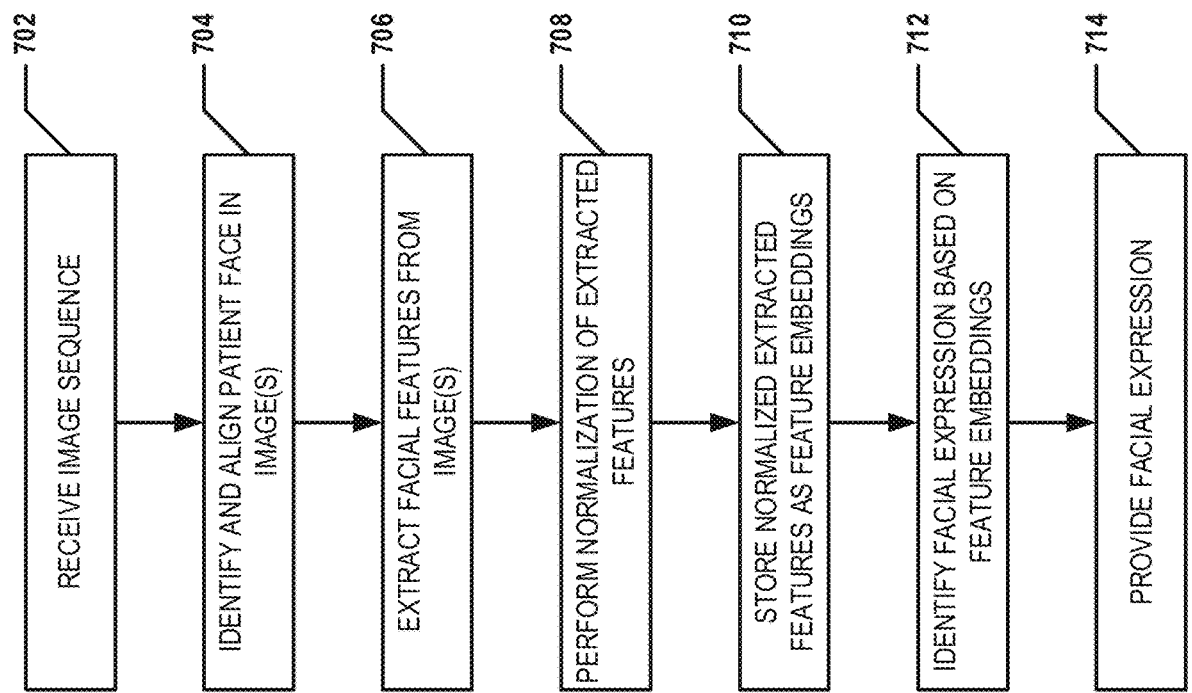

FIG. 7 provides a flowchart illustrating various processes, procedures, and/or operations performed, for example by an analysis computing entity, for providing patient facial expression information/data according to an example embodiment.

Figure 7A:
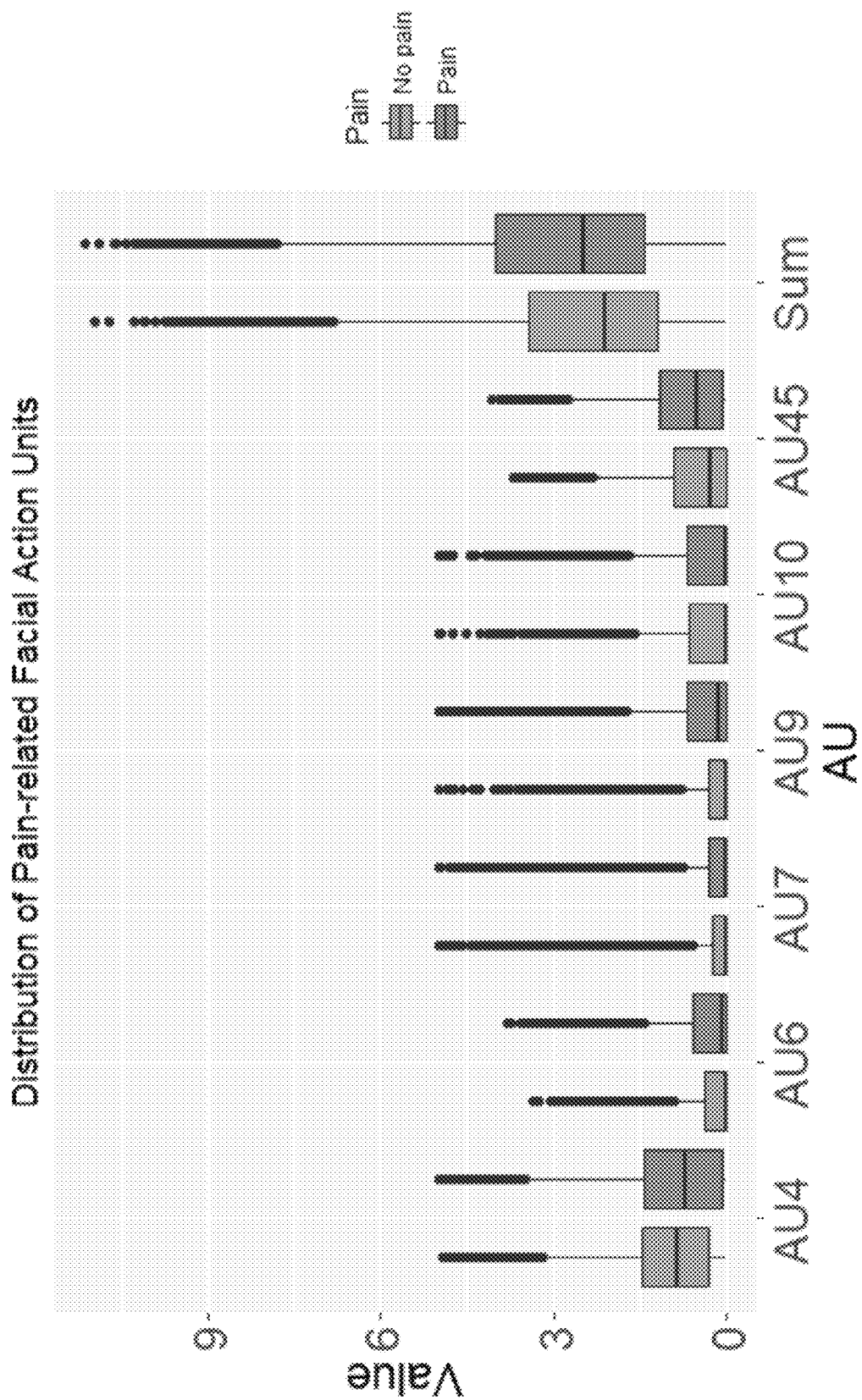

FIG. 7A provides a plot illustrating the observed distribution of facial action units for patients experiencing pain and patients not experiencing pain for a group of patients observed using a patient monitoring system in accordance with the present invention.

Figure 8:
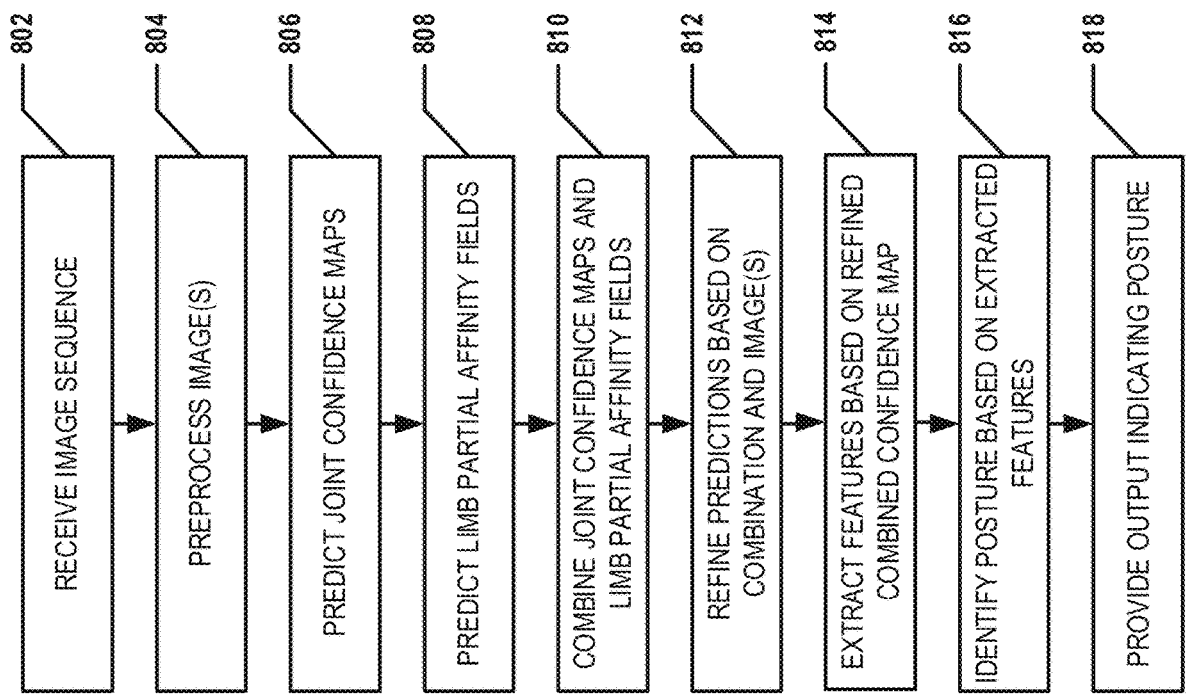

FIG. 8 provides a flowchart illustrating various processes, procedures, and/or operations performed, for example by an analysis computing entity, for providing patient posture information/data according to an example embodiment.

Figure 8A:
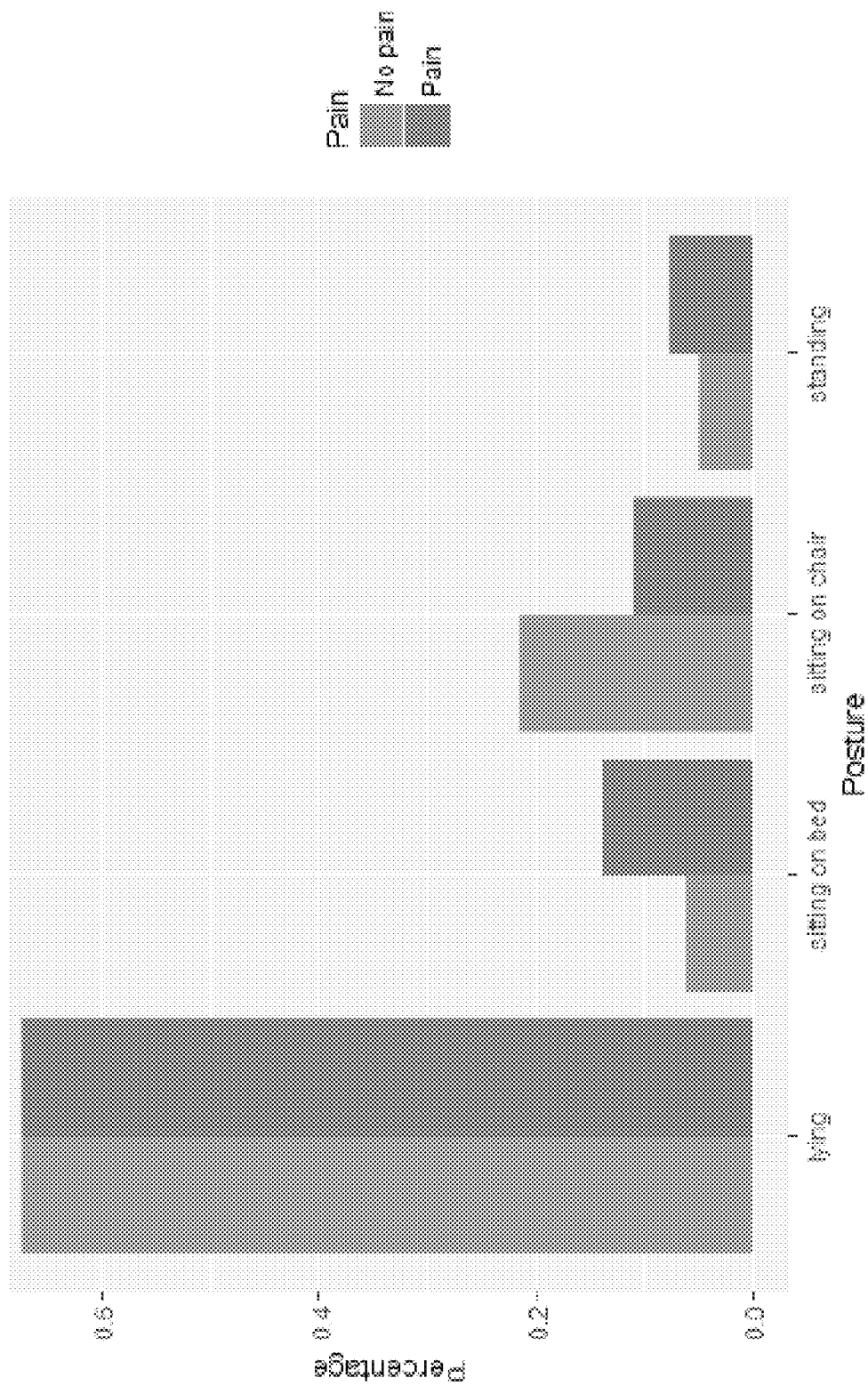

FIG. 8A provides a plot illustrating the observed distribution of body postures for patients experiencing pain and patients not experiencing pain for a group of patients observed using a patient monitoring system in accordance with the present invention.

DETAILED DESCRIPTION

Various embodiments of the present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. The term "or" is used herein in both the alternative and conjunctive sense, unless otherwise indicated. The terms "illustrative" and "exemplary" are used to be examples with no indication of quality level. Like numbers refer to like elements throughout.

I. Computer Program Products, Methods, and Computing Entities

Embodiments of the present invention may be implemented in various ways, including as computer program products that comprise articles of manufacture. A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatus, systems, computing devices, computing entities, and/or the like. As such, embodiments of the present invention may take the form of an apparatus, system, computing device, computing entity, and/or the like executing instructions stored on a computer-readable storage medium to perform certain steps or operations. Thus, embodiments of the present invention may also take the form of an entirely hardware embodiment, an entirely computer program product embodiment, and/or an embodiment that comprises combination of computer program products and hardware performing certain steps or operations.

Embodiments of the present invention are described below with reference to block diagrams and/or flowchart illustrations. Thus, it should be understood that each block of the block diagrams and/or flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

II. Exemplary System Architecture

Figure 1:
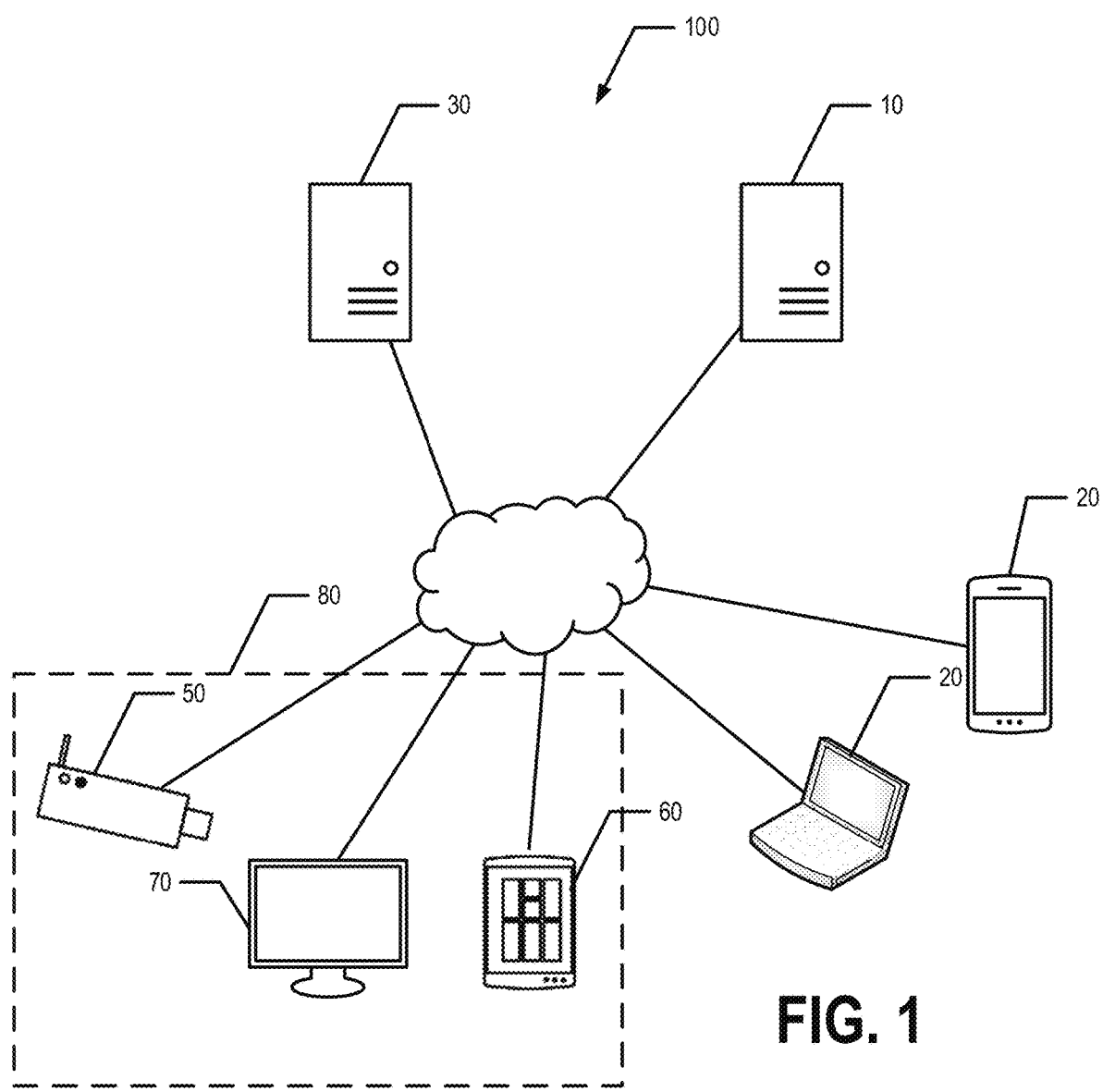
FIG. 1 is an overview of a system that can be used to practice embodiments of the present invention.

FIG. 1 provides an illustration of an exemplary embodiment of the present invention. As shown in FIG. 1, this particular embodiment may include one or more analysis computing entities 10, one or more user computing entities 20, one or more information/data hosting entities 30, one or more networks 40, one or more patient monitoring systems 80, and/or the like. In various embodiments, each patient monitoring system 80 includes one or more sensors, such as a visual sensor (e.g., camera 50), an accelerometer, a light sensor, a sound sensor (e.g., encompassed within sensing device 60), in-room display 70, and/or the like. In an example embodiment, components of a patient monitoring system 80 may be mounted within a patient room and configured to monitor a patient and the environment about the patient. Each of these components, entities, devices, systems, and similar words used herein interchangeably may be in direct or indirect communication with, for example, one another over the same or different wired or wireless networks. Additionally, while FIG. 1 illustrates the various system entities as separate, standalone entities, the various embodiments are not limited to this particular architecture.

1. Exemplary Analysis Computing Entity

Figure 2:
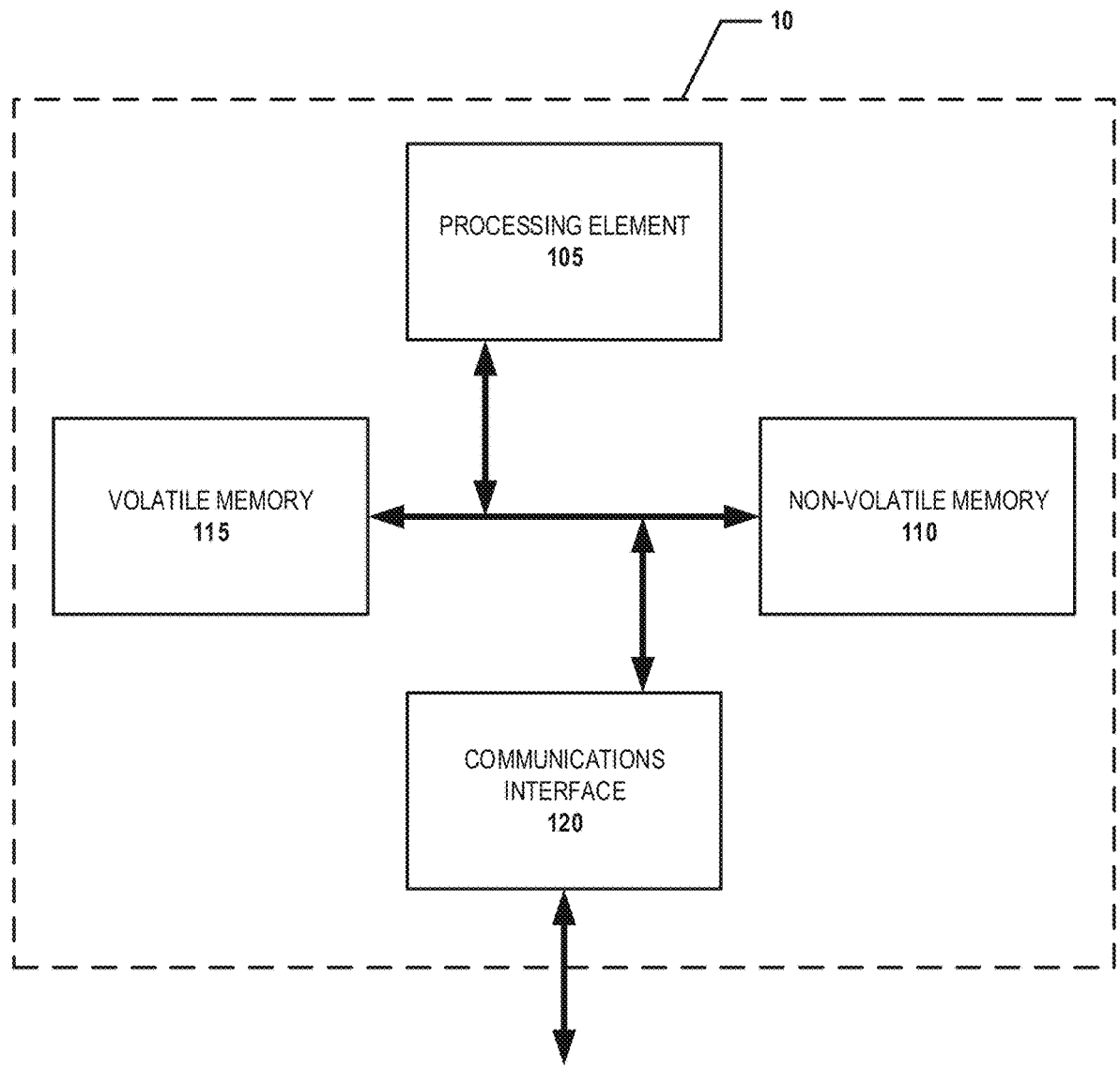
FIG. 2 is an exemplary schematic diagram of an analysis computing entity according to one embodiment of the present invention.

FIG. 2 provides a schematic of an analysis computing entity 10 according to one embodiment of the present invention. In example embodiments, an analysis computing entity 10 may be configured to implement a machine-learning based framework for receiving raw patient data received from a plurality of sensors (e.g., camera 50 and/or sensing device 60) and for determining physiological patient characteristics, such as whether the patient is delirious, that may be provided via output patient data from the analysis computing entity 10. In an example embodiment, the analysis computing entity 10 may be configured to monitor various aspects of the environment about one or more patients (e.g., light levels, noise levels, frequency of the presence of individuals and/or care providers within the patient room, and/or the like). In various embodiments, the analysis computing entity 10 may be configured to provide patient information/data, an alert regarding a patient, and/or the like such that a care provider may be review patient information/data, receive an alert regarding a patient and/or such that a patient record (e.g., electronic health record) for a patient may be updated based on the patient information/data.

In general, the terms computing entity, computer, entity, device, system, and/or similar words used herein interchangeably may refer to, for example, one or more computers, computing entities, desktops, mobile phones, tablets, phablets, notebooks, laptops, distributed systems, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

In one embodiment, the analysis computing entity 10 may also include one or more communications interfaces 120 for communicating with various other computing entities, such as by communicating data, content, information, and/or similar terms used herein interchangeably that can be transmitted, received, operated on, processed, displayed, stored, and/or the like.

As shown in FIG. 2, in one embodiment, the analysis computing entity 10 may include or be in communication with one or more processing elements 105 (also referred to as processors, processing circuitry, and/or similar terms used herein interchangeably) that communicate with other elements within the analysis computing entity 10 via a bus, for example. As will be understood, the processing element 105 may be embodied in a number of different ways. For example, the processing element 105 may be embodied as one or more complex programmable logic devices (CPLDs), microprocessors, multi-core processors, co-processing entities, application-specific instruction-set processors (ASIPs), microcontrollers, and/or controllers. Further, the processing element 105 may be embodied as one or more other processing devices or circuitry. The term circuitry may refer to an entirely hardware embodiment or a combination of hardware and computer program products. Thus, the processing element 105 may be embodied as integrated circuits, application specific integrated circuits (ASICs), field programmable gate arrays (FPGAs), programmable logic arrays (PLAs), hardware accelerators, other circuitry, and/or the like. As will therefore be understood, the processing element 105 may be configured for a particular use or configured to execute instructions stored in volatile or non-volatile media or otherwise accessible to the processing element 105. As such, whether configured by hardware or computer program products, or by a combination thereof, the processing element 105 may be capable of performing steps or operations according to embodiments of the present invention when configured accordingly.

In one embodiment, the analysis computing entity 10 may further include or be in communication with non-volatile media (also referred to as non-volatile storage, memory, memory storage, memory circuitry and/or similar terms used herein interchangeably). In one embodiment, the non-volatile storage or memory may include one or more non-volatile storage or memory media 110, including but not limited to hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. As will be recognized, the non-volatile storage or memory media may store databases, database instances, database management systems, data, applications, programs, program modules, scripts, source code, object code, byte code, compiled code, interpreted code, machine code, executable instructions, and/or the like. The term database, database instance, database management system, and/or similar terms used herein interchangeably may refer to a collection of records or data that is stored in a computer-readable storage medium using one or more database models, such as a hierarchical database model, network model, relational model, entity—relationship model, object model, document model, semantic model, graph model, and/or the like.

In one embodiment, the analysis computing entity 10 may further include or be in communication with volatile media (also referred to as volatile storage, memory, memory storage, memory circuitry and/or similar terms used herein interchangeably). In one embodiment, the volatile storage or memory may also include one or more volatile storage or memory media 115, including but not limited to RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. As will be recognized, the volatile storage or memory media may be used to store at least portions of the databases, database instances, database management systems, data, applications, programs, program modules, scripts, source code, object code, byte code, compiled code, interpreted code, machine code, executable instructions, and/or the like being executed by, for example, the processing element 105. Thus, the databases, database instances, database management systems, data, applications, programs, program modules, scripts, source code, object code, byte code, compiled code, interpreted code, machine code, executable instructions, and/or the like may be used to control certain aspects of the operation of the analysis computing entity 10 with the assistance of the processing element 105 and operating system.

As indicated, in one embodiment, the analysis computing entity 10 may also include one or more communications interfaces 120 for communicating with various other computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOC SIS), or any other wired transmission protocol. Similarly, the analysis computing entity 10 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra wideband (UWB), infrared (IR) protocols, near field communication (NFC) protocols, Wibree, Bluetooth protocols, wireless universal serial bus (USB) protocols, and/or any other wireless protocol.

Although not shown in FIG. 2, the analysis computing entity 10 may also comprise a user interface (that can include a display coupled to a processing element). For example, the user interface may include or be in communication with one or more input elements, such as a keyboard input, a mouse input, a touch screen/display input, motion input, movement input, audio input, pointing device input, joystick input, keypad input, and/or the like. The analysis computing entity 10 may also include or be in communication with one or more output elements (not shown), such as audio output, video output, screen/display output, motion output, movement output, and/or the like. These input and output elements may include software components such as a user application, browser, graphical user interface, and/or the like to facilitate interactions with and/or cause display of information/data from the analysis computing entity 10, as described herein. The user input interface can comprise any of a number of devices or interfaces allowing the user computing entity 20 to receive data, such as a keypad (hard or soft), a touch display, voice/speech or motion interfaces, or other input device. In embodiments including a keypad, the keypad can include (or cause display of) the conventional numeric (0-9) and related keys (#, *), and other keys used for operating the user computing entity 20 and may include a full set of alphabetic keys or set of keys that may be activated to provide a full set of alphanumeric keys.

As will be appreciated, one or more of the components of the analysis computing entity may be located remotely from other components of the analysis computing entity 10, such as in a distributed system. Furthermore, one or more of these components may be combined with additional components to perform various functions described herein, and these additional components may also be included in the analysis computing entity 10. Thus, the analysis computing entity 10 can be adapted to accommodate a variety of needs and circumstances. As will be recognized, these architectures and descriptions are provided for exemplary purposes only and are not limiting to the various embodiments.

2. Exemplary User Computing Entity

In various embodiments, a user computing entity 20 may be configured to exchange and/or store information/data with the analysis computing entity 10. For instance, the user computing entity 20 may be used by a user (e.g., a doctor, a nurse, and/or another care provider, a scientist, a lab technician, an administrator, and/or the like) to provide instructions to the analysis computing entity 10 for structuring or modifying the analysis to be performed by the analysis computing entity 10. The user computing entity 20 may additionally or alternatively receive information/data and/or alerts from the analysis computing entity 10 or an information/data hosting entity 30 regarding results produced from the operations performed by the analysis computing entity 10. For example, a user computing entity 20 may receive data indicative of a patient's current state from the analysis computing entity 10 to provide the same to a care provider.

In one embodiment, the user computing entity 20 may include one or more components that are functionally similar to those of the analysis computing entity 10 described above. For example, in one embodiment, each user computing entity 20 may include one or more processing elements (e.g., CPLDs, microprocessors, multi-core processors, co-processing entities, ASIPs, microcontrollers, and/or controllers), volatile and non-volatile storage or memory, one or more communications interfaces, and/or one or more user interfaces.

Figure 3:
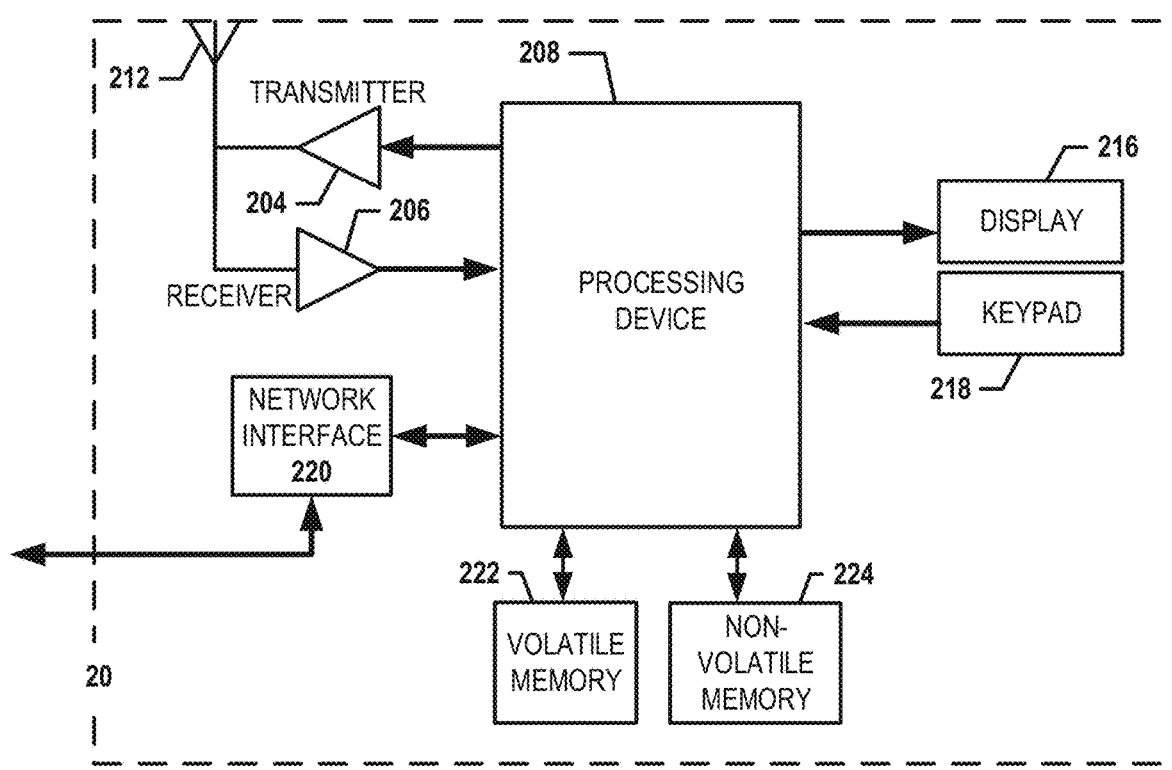
FIG. 3 is an exemplary schematic diagram of a user computing entity according to one embodiment of the present invention.

FIG. 3 provides an illustrative schematic representative of a user computing entity 20 that can be used in conjunction with embodiments of the present invention. In general, the terms device, system, computing entity, entity, and/or similar words used herein interchangeably may refer to, for example, one or more computers, computing entities, desktops, mobile phones, tablets, phablets, notebooks, laptops, distributed systems, wearables, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. User computing entities 20 can be operated by various parties. As shown in FIG. 3, the user computing entity 20 can include an antenna 212, a transmitter 304 (e.g., radio), a receiver 206 (e.g., radio), and a processing device 208 (e.g., CPLDs, microprocessors, multi-core processors, coprocessing entities, ASIPs, microcontrollers, and/or controllers) that provides signals to and receives signals from the transmitter 204 and receiver 206, respectively.

The signals provided to and received from the transmitter 204 and the receiver 206, respectively, may include signaling information in accordance with air interface standards of applicable wireless systems. In this regard, the user computing entity 20 may be capable of operating with one or more air interface standards, communication protocols, modulation types, and access types. More particularly, the user computing entity 20 may operate in accordance with any of a number of wireless communication standards and protocols, such as those described above with regard to the analysis computing entity 10. In a particular embodiment, the user computing entity 20 may operate in accordance with multiple wireless communication standards and protocols, such as UMTS, CDMA2000, 1×RTT, WCDMA, TD-SCDMA, LTE, E-UTRAN, EVDO, HSPA, HSDPA, Wi-Fi, Wi-Fi Direct, WiMAX, UWB, IR, NFC, Bluetooth, USB, and/or the like. Similarly, the user computing entity 20 may operate in accordance with multiple wired communication standards and protocols, such as those described above with regard to the analysis computing entity 10 via a network interface 220.

Via these communication standards and protocols, the user computing entity 20 can communicate with various other entities using concepts such as Unstructured Supplementary Service Data (USSD), Short Message Service (SMS), Multimedia Messaging Service (MMS), Dual-Tone Multi-Frequency Signaling (DTMF), and/or Subscriber Identity Module Dialer (SIM dialer). The user computing entity 20 can also download changes, add-ons, and updates, for instance, to its firmware, software (e.g., including executable instructions, applications, program modules), and operating system.

According to one embodiment, the user computing entity 20 may include location determining aspects, devices, modules, functionalities, and/or similar words used herein interchangeably. For example, the user computing entity 20 may include outdoor positioning aspects, such as a location module adapted to acquire, for example, latitude, longitude, altitude, geocode, course, direction, heading, speed, universal time (UTC), date, and/or various other information/data. In one embodiment, the location module can acquire data, sometimes known as ephemeris data, by identifying the number of satellites in view and the relative positions of those satellites. The satellites may be a variety of different satellites, including Low Earth Orbit (LEO) satellite systems, Department of Defense (DOD) satellite systems, the European Union Galileo positioning systems, the Chinese Compass navigation systems, Indian Regional Navigational satellite systems, and/or the like. Alternatively, the location information can be determined by triangulating the user computing entity's 20 position in connection with a variety of other systems, including cellular towers, Wi-Fi access points, and/or the like. Similarly, the user computing entity 20 may include indoor positioning aspects, such as a location module adapted to acquire, for example, latitude, longitude, altitude, geocode, course, direction, heading, speed, time, date, and/or various other information/data. Some of the indoor systems may use various position or location technologies including RFID tags, indoor beacons or transmitters, Wi-Fi access points, cellular towers, nearby computing devices (e.g., smartphones, laptops) and/or the like. For instance, such technologies may include the iBeacons, Gimbal proximity beacons, Bluetooth Low Energy (BLE) transmitters, NFC transmitters, and/or the like. These indoor positioning aspects can be used in a variety of settings to determine the location of someone or something to within inches or centimeters.

The user computing entity 20 may also comprise a user interface (that can include a display 216 coupled to a processing device 208) and/or a user input interface (coupled to a processing device 208). For example, the user interface may be configured to provide a user application, browser, interactive user interface, and/or similar words used herein interchangeably executing on and/or accessible via the user computing entity 20 to interact with and/or cause display of information from the analysis computing entity 10, as described herein. The user input interface can comprise any of a number of devices or interfaces allowing the user computing entity 20 to receive data, such as a keypad 218 (hard or soft), a touch display, voice/speech or motion interfaces, or other input device. In embodiments including a keypad 218, the keypad 218 can include (or cause display of) the conventional numeric (0-9) and related keys (#, *), and other keys used for operating the user computing entity 20 and may include a full set of alphabetic keys or set of keys that may be activated to provide a full set of alphanumeric keys. In addition to providing input, the user input interface can be used, for example, to activate or deactivate certain functions, such as screen savers and/or sleep modes.

The user computing entity 20 can also include volatile storage or memory 222 and/or non-volatile storage or memory 224, which can be embedded and/or may be removable. For example, the non-volatile memory may be ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. The volatile and non-volatile storage or memory can store databases, database instances, database management systems, data, applications, programs, program modules, scripts, source code, object code, byte code, compiled code, interpreted code, machine code, executable instructions, and/or the like to implement the functions of the user computing entity 20. As indicated, this may include a user application that is resident on the entity or accessible through a browser or other user interface for communicating with the analysis computing entity 10 and/or various other computing entities.

In another embodiment, the user computing entity 20 may include one or more components or functionality that are the same or similar to those of the analysis computing entity 10, as described in greater detail above. As will be recognized, these architectures and descriptions are provided for exemplary purposes only and are not limiting to the various embodiments. In an example embodiment, the functions described as being performed by the user computing entity 20 are performed by the analysis computing entity 10 and/or the user computing entity 20 may be a client (e.g., a thin client) of the analysis computing entity 10. For example, if the informant computing entity 100 is a data collection system configured to capture weather information/data or sunspot information/data, for example, the user computing entity 20 may be a user facing portion of the data collection system.

4. Exemplary Index Information/Data Hosting Entity

In various embodiments, the index information/data computing entity 30 may be configured to receive, store, and/or provide information/data utilized and/or generated by the automated, machine-learning framework discussed herein. For example, raw patient data generated by the one or more sensors (e.g., camera 50, sensing devices 60, and/or the like) may be stored via the index information/data computing entity 30 and selectably retrieved by the analysis computing entity 10 as needed. Moreover, the results data generated by the analysis computing entity 10 may be stored via the index information/data computing entity 30 for archiving, indexing, and/or later retrieval, as needed. In an example embodiment, the index information/data computing entity 30 may store electronic health records and/or other patient records in a secure manner (e.g., in a secured and/or encrypted patient record database and/or the like).

In one embodiment, an index information/data computing entity 30 may include one or more components that are functionally similar to those of the analysis computing entity 10, user computing entity 20, and/or the like. For example, in one embodiment, each index information/data computing entity 30 may include one or more processing elements (e.g., CPLDs, microprocessors, multi-core processors, co-processing entities, ASIPs, microcontrollers, and/or controllers), volatile and non-volatile storage or memory, one or more communications interfaces, and/or one or more user interfaces.

5. Exemplary Visual Sensors

In various embodiments, visual sensors, such as video cameras, still cameras, and/or the like may be configured to record patient movement, facial expressions, and/or the like of a patient. These visual sensors (e.g., cameras 50) may be configured to continuously record visual images (e.g., via a 30 frames per second data recordation frequency, although other framerates may be utilized) of the patient. The visual sensors may have associated motion sensors that may be utilized to generate trigger signals to initiate data recordation in embodiments without continuous recording. Moreover, the visual sensors may comprise one or more pivots and/or movement features (e.g., automated movement features) to enable patient tracking when moving outside of the field of view of the camera (e.g., a 90 degree field of view).

Moreover, in certain embodiments, the visual sensors may include one or more components that are functionally similar to those of the analysis computing entity 10, user computing entity 20, and/or the like. For example, in one embodiment, each visual sensor may include one or more processing elements (e.g., CPLDs, microprocessors, multi-core processors, co-processing entities, ASIPs, microcontrollers, and/or controllers), volatile and non-volatile storage or memory, one or more communications interfaces, and/or one or more user interfaces.

6. Exemplary Sensing Device

Moreover, various embodiments comprise one or more additional sensing devices, such as accelerometers, sound sensors, light sensors, pressure sensors, and/or the like. These sensors may be embodied within one or more sensing devices 60, and each sensing device 60 may comprise one or more sensors (e.g., various combinations of sensors). For example, a single sensing device 60 may comprise a light sensor and a sound sensor.

In certain embodiments, various sensing devices 60 may be wearable by a patient (e.g., wearable sensors). The sensing devices 60 may thus comprise one or more bands, straps, adhesives, and/or other securing features such that the sensing device 60 may be secured onto the patient. As a specific example of a wearable sensor, a sensing device 60 comprising an accelerometer may be configured to be secured onto a patient via a wrist strap, an arm strap, an ankle strap, a chest strap, and/or the like.

Moreover, the sensing devices 60 may each include one or more components that are functionally similar to those of the analysis computing entity 10, user computing entity 20, and/or the like. For example, in one embodiment, each sensing device 60 may include one or more processing elements (e.g., CPLDs, microprocessors, multi-core processors, co-processing entities, ASIPs, microcontrollers, and/or controllers), volatile and non-volatile storage or memory, one or more communications interfaces, and/or one or more user interfaces.

III. Exemplary System Operation

Example embodiments of the present invention provide tools for automatically determining patient physiological conditions based at least in part on raw patient data collected and/or generated by the one or more sensors (e.g., visual sensors 50 and/or sensing devices 60). Certain example embodiments utilize an automated analytics framework to implement a machine-learning based algorithm for determining patient physiological characteristics based on patient activities (e.g., movements, expressions, and/or the like) recorded within the raw patient data.

Figure 4:
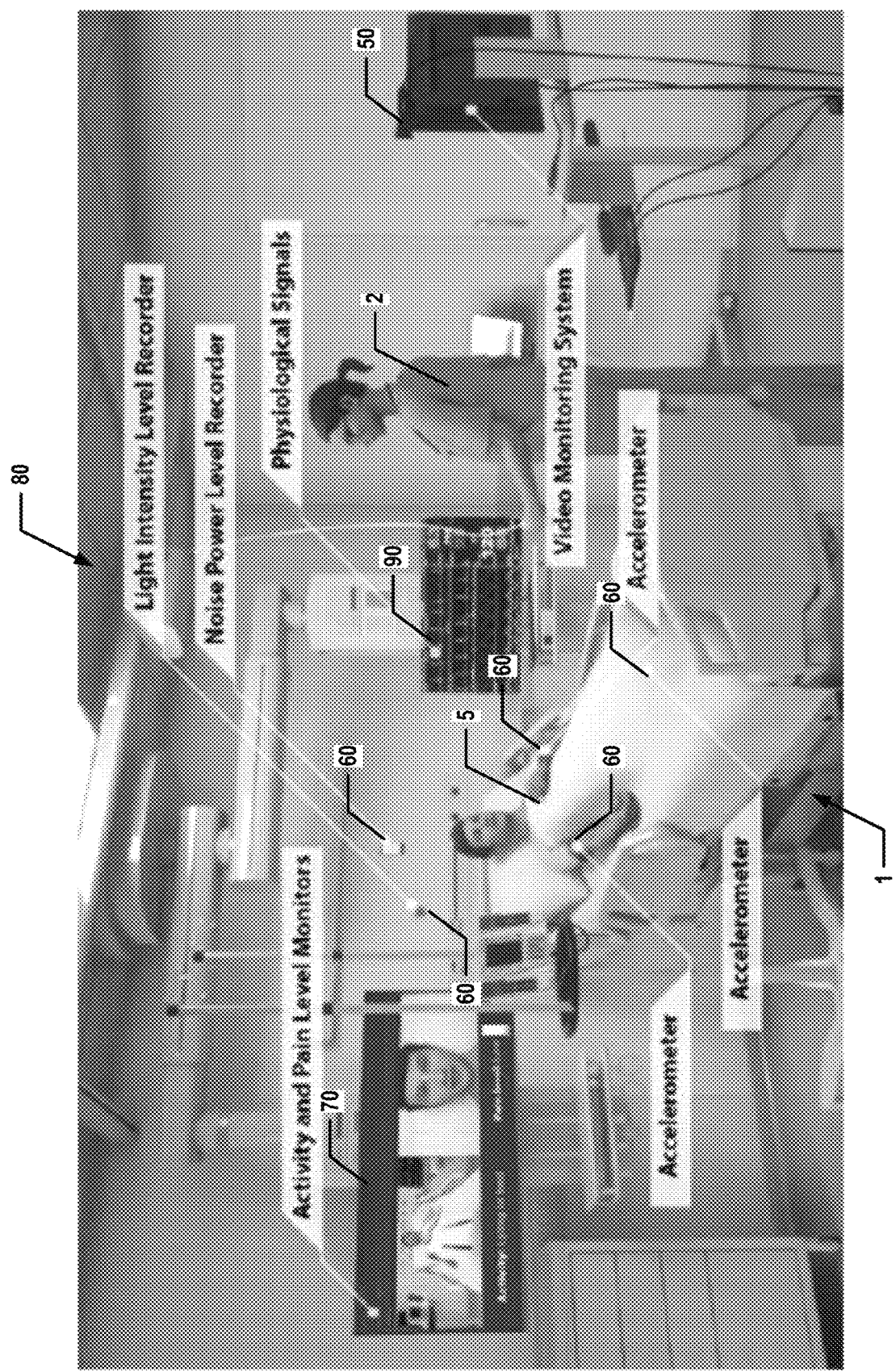
FIG. 4 illustrates an example patient monitoring system according to one embodiment of the present invention.

FIG. 4 illustrates an example patient monitoring system 80. In the illustrated embodiment, the patient monitoring system 80 comprises components disposed in a patient room 1 for patient 5. In various embodiments, the patient monitoring system 80 comprises one or more sensing devices 60 configured to monitor and/or capture patient surroundings information/data regarding the patient room 1. For example, the patient monitoring system 80 comprises one or more sensing devices 60 configured to determine and/or monitor a light level within the patient room 1, a noise level within the patient room 1, the presence of individuals other than the patient 5 within the room (e.g., care provider 2, and/or the like), and/or other patient surroundings information/data corresponding to the environment about the patient 5 (e.g., within the patient room 1). In an example embodiment, the one or more sensing devices 60 configured to determine and/or monitor a light level within the patient room 1, noise level within the patient room 1, and/or the like are positioned near the patient's 5 head such that the determined and/or monitored light level, noise reminder, and/or the like is similar to that experienced by the patient 5. For example, the patient monitoring system 80 comprises one or more sensor devices 60 that are wearable sensors. For example, the wearable sensors may be secured (e.g., via a wrist/arm/leg/ankle/chest strap, adhesive, and/or the like). In an example embodiment, the wearable sensors comprise accelerometers and/or other sensors configured to monitor the movement of patient. In an example embodiment, the wearable sensors may further comprise other sensors configured to capture biometric information/data for the patient and/or other patient information/data. In an example embodiment, the patient 5 may wear a wearable sensor secured to at least one of the patient's wrist, arm, leg, ankle, or chest. In various embodiments, the sensing devices 60 are configured to capture patient surroundings information/data and/or wearable information/data and provide the patient surroundings information/data and/or wearable information/data (e.g., via network 40) such that an analysis computing entity 10 receives the patient surroundings information/data and/or wearable information/data.

In various embodiments, the patient monitoring system 80 comprises one or more visual sensors 50. For example, the visual sensors 50 may include one or more still cameras configured to periodically (e.g., every ten seconds, every thirty seconds, every minute, every two minutes, every five minutes, and/or the like), regularly, and/or in a triggered manner (e.g., based on a motion sensor triggering and/or the like) capture a digital image of the patient 5 and/or the environment about the patient (e.g., at least a portion of the patient room 1). In an example embodiment, the visual sensors 50 may include one or more video cameras configured to capture a stream of digital images of the patient 5 and/or the environment about the patient (e.g., at least a portion of the patient room 1) in accordance with a preset frame rate. Thus, in various embodiments, the visual sensor (s) 50 of a patient monitoring system 80 each capture a sequence of digital images of the patient 5 and/or the environment about the patient (e.g., at least a portion of the patient room 1). In various embodiments, the visual sensors 50 are configured to provide the sequence of digital images of the patient 5 and/or the environment about the patient (e.g., at least a portion of the patient room 1) (e.g., via the network 40) such that an analysis computing entity 10 receives the sequence of digital images.

In various embodiments, the patient monitoring system further comprises an in-room display 70. In various embodiments, the in-room display 70 is configured to display various patient information/data, patient surroundings information/data, and/or the like. In an example embodiment, the in-room display 70 is a thin client of the analysis computing entity 10. For example, the analysis computing entity 10 may be configured to receive wearable information/data, patient surroundings information/data, one or more sequences of digital images regarding the patient 5 and/or the environment about the patient (e.g., at least a portion of the patient room 1), determine patient information/data and/or environment information/data, and provide at least a portion of the patient information/data and/or environment information/data such that patient information/data and/or environment information/data is displayed by the in-room display 70.

In various embodiments, the patient monitoring system may comprise one or more physiological sensors and/or a physiological sensor display 90. For example, as noted above one or more wearable sensors may be configured for capturing and providing biometric information/data corresponding to the patient 5 (e.g., heart rate, temperature, oxygen saturation level, blood pressure, respiratory rate, and/or the like). Various other sensors may be used to capture any variety of biometric and/or physiological information/data corresponding to the patient 5. In various embodiments, physiological sensor display is configured to provide a visualization of one or more biometric and/or physiological parameters of the captured biometric and/or physiological information/data corresponding to the patient 5.

FIG. 5 provides a schematic diagram of the information/data captured and/or available to care providers via manual patient monitoring and automated patient monitoring according to an example embodiment. For example, via a manual monitoring system used in conjunction and/or alongside a patient monitoring system, patient physiological information/data may be captured (e.g., heart rate, temperature, oxygen saturation level, blood pressure, respiratory rate, and/or the like) and provided to a care provider (e.g., via physiological sensor display 90). In another example, via a manual monitoring system, a care provider may access information/data regarding the patient, the patient's medical history, and/or the like, via an electronic health record corresponding to the patient. In an example embodiment, the analysis computing entity 10 is configured to provide patient information/data that may be used to update a patient record, such as an electronic health record. In an example embodiment, the analysis computing entity 10 may provide a suggestion and/or ask for care provider approval for updating an electronic health record corresponding to a patient based on patient information/data and/or environmental information/data determined based on received wearable information/data and/or patient surroundings information/data. In another example, via a manual monitoring system, a care provider may use one or more questionnaires to gather information/data regarding a patient's pain level, efficacy of one or more treatments, patient's care experience, and/or the like.

In various embodiments, the patient monitoring system 80 and an analysis computing entity 10 provide an automated monitoring system for monitoring a patient 5. For example, an automated monitoring system may comprise patient monitoring system 80 such that the automated monitoring system configured to automatically capture one or more sequences of images of the patient and/or the environment about the patient (e.g., at least a portion of patient room 1) via one or more visual sensors 50, capture wearable information/data via patient mounted sensing devices 60, capture patient surroundings information/data corresponding to light level and/or sound level in the environment about the patient (e.g., at least a portion of patient room 1). An analysis computing entity 10 of the automated monitoring system may receive and analyze the wearable information/data, patient surrounding information/data, and/or other information/data corresponding to the patient and provide patient and/or environment information/data for review by a care provider 2 and/or for inclusion in a patient record. In an example embodiment, the analysis computing entity 10 is further configured to provide one or more alerts (e.g., such that a user computing entity 20 receives the alerts and provides a user-perceivable notification of the receipt of the alert) in response to determining that a trigger event has occurred. In an example embodiment, the patient information/data comprises face detection information/data, face recognition information/data, facial action unites (AU) information/data, facial expression information/data, head pose information/data, posture information/data, actigraphy information/data, and/or the like. In an example embodiment, the environment information/data comprises light level information/data, noise level information/data, visitation frequency information/data, and/or the like.

Providing Patient Information/Data and/or an Alert

FIG. 6 provides a flowchart illustrating various processes, procedures, operations, and/or the like for providing patient information/data and/or an alert regarding a patient. Starting at block 602, sensor information/data (e.g., wearable information/data, patient surroundings information/data, and/or sequence(s) of images of the patient and/or environment about the patient) are received. For example, the analysis computing entity 10 may receive (e.g., via communication interface 120) sensor information/data (e.g., wearable information/data, patient surroundings information/data, and/or sequence(s) of images of the patient and/or environment about the patient). For example, sensing devices 60 and visual sensors 50 may capture sensor information/data comprising wearable information/data, patient surroundings information/data, and/or sequence(s) of images of the patient and/or environment about the patient. In an example embodiment, a patient identifier and/or sensor identifier is received with the sensor information/data. For example, sensing devices 60 and visual sensors 50 may provide a patient identifier and/or sensor identifier along with sensor information/data.

At block 604, the sensor information/data is analyzed. For example, the analysis computing entity 10 analyzes the sensor information/data. For example, the memory 110, 115 may store computer program code and execute portions of the computer program code with the processing element 105 to cause the analysis computing entity 10 to analyze the sensor information/data. For example, the sensor information/data may be analyzed to determine patient information/data and/or environment information/data.

For example, the sequence(s) of images of the patient and/or environment about the patient may be analyzed (e.g., using face detection computer program code) to detect one or more faces in one or more images of the sequence(s) of images. For example, one or more faces detected within the sequence(s) of images may be analyzed (e.g., using face recognition computer program code) to determine if one of the detected faces is the face of the patient. For example, a face that has been identified as the face of the patient within the sequence(s) of images may be analyzed (e.g., using facial AU detection computer program code) to identify facial AUs of the patient. For example, a face that has been identified as the face of the patient within the sequence(s) of images may be analyzed (e.g., using facial expression detection computer program code) to identify facial expressions of the patient. For example, a face that has been identified as the face of the patient and the corresponding head within the sequence(s) of images may be analyzed (e.g., using head position detection computer program code) to identify a head position of the patient. For example, a roll (e.g., rotation in plane), pitch (e.g., up and down), and yaw (e.g., side to side) corresponding to the patient's head may be determined and the head position may be provided as roll, pitch, and yaw at a particular time. For example, the body associated with a face that has been identified as the face of the patient within the sequence(s) of images (e.g., using posture recognition computer program code) to identify a body posture (e.g., laying down, sitting in bed, sitting in a chair, standing) of the patient. For example, the wearable information/data may comprise movement information/data captured by one or more accelerometers or other movement sensor of the one or more wearable sensors. The movement information/data may be analyzed (e.g., using actigraphy computer program code) to determine activity information/data of the patient. Thus, in various embodiments, patient information/data (e.g., facial AUs, facial expressions, head position, body posture, activity information/data and/or the like) may be determined by analyzing the sensor information/data (e.g., wearable information/data and/or one or more images of a sequence of images of the patient and/or environment about the patient).

In an example embodiment, the sensor information/data comprises patient surrounding information/data. The patient surrounding information/data may be analyzed (e.g., using light level computer program code and/or noise level computer program code) to determine a light level and/or noise level in the environment about the patient (e.g., in the patient room). In an example embodiment, one or more images of a sequence of images of the patient and/or environment about the patient may be analyzed (e.g., using light level computer program code) to determine a light level in the environment about the patient. In an example embodiment, the sequence of images may be associated with audio information/data (e.g., the sequence of images may be a video including image and audio information/data. For example, the audio information/data may be analyzed (e.g., using noise level computer program code) to determine a noise level in the environment about the patient. In an example embodiment, one or more images of the sequence of images of the patient and/or the environment about the patient may be analyzed (e.g., using face detection and/or facial recognition computer program code) to identify when one or more individuals other than the patient (e.g., care providers, family members, and/or other visitors) are present in the patient room. For example, visitor information/data including the frequency, amount of time, percentage/fraction of time and/or the like that one or more individuals other than the patient (e.g., care providers, family members, and/or other visitors) are present in the patient room may be determined. In an example embodiment, the presence of one or more individuals other than the patient in the patient room may be identified based on audio information/data and/or sensor information/data corresponding to noise and/or sounds within the patient room. In various embodiments, the patient surrounding information/data and/or one or more images of the sequence of images may be analyzed to determine environment information/data such as light level information/data, noise level information/data and/or visitor information/data.

Thus, in various embodiments, the sensor information/data (e.g., wearable information/data and/or patient surroundings information/data captured and provided by the sensing devices and/or one or more images of a sequence of images of the patient and/or the environment about the patient captured and provided by visual sensor 50) may be analyzed to determine patient information/data and/or environment information/data.

In various embodiments, the patient information/data and/or environment information/data is associated with a patient identifier. In an example embodiment, the sensor information/data is received in associated with a patient identifier and the patient identifier is associated with the patient information/data and/or environment information/data determined by analyzing the sensor information/data. In an example embodiment, the sensor information/data is received in association with one or more sensor identifiers that identify sensors having known locations (e.g., a patient room number). A patient identifier for a patient assigned and/or corresponding to the known location corresponding to the sensor identifiers may be identified and associated with the patient information/data and/or environment information/data determined by analyzing the sensor information/data. In an example embodiment, a face recognition analysis is performed on at least one image of an image sequence of the patient and/or environment about the patient and a patient identifier identifying the patient shown in the image(s) is identified based on the recognition of the patient's face. The patient identifier is then associated with the patient information/data and/or environment information/data determined by analyzing the sensor information/data.

At block 606, the patient information/data and/or environment information/data is provided. For example, the analysis computing entity 10 may provide (e.g., via communications interface 120) patient information/data and/or environment information/data. For example, the analysis computing entity 10 may provide at least a portion of the patient information/data and/or environment information/data determined at block 604 such that the at least a portion of the patient information/data and/or environment information/data is received by a user computing entity 20, index information/data computing entity 30, and/or in-room display 70. In various embodiments, the patient information/data and/or environment information/data may be provided in association with a patient identifier. In various embodiments, the patient information/data and/or environment information/data is objective data corresponding to the patient and the environment about the patient.

For example, patient information/data and/or environment information/data may be received by an in-room display 70 corresponding to a patient identifier corresponding to the sensor information/data and/or a location identifier corresponding to one or more sensor identifiers corresponding to the sensor information/data. The in-room display 70 may process the received patient information/data and/or environment information/data and provide (e.g., display) at least a portion of the received patient information/data and/or environment information/data. For example, the in-room display 70 may provide an interactive user interface that a care provider may use to view patient information/data and/or environment information/data corresponding to the patient located within the same patient room 1 as the in-room display 70.

For example, patient information/data and/or environment information/data may be received by a user computing entity 20 corresponding to a care provider or other user associated with the patient (e.g., assigned to the patient and/or the like). In an example embodiment, the user computing entity 20 may provide an interactive user interface through which a user may access patient information/data and/or environment information/data corresponding to a patient. In an example embodiment, the user may interact with the interactive user interface to view the patient information/data and/or environment information/data for a patient. In an example embodiment, the user computing entity 20 may access patient information/data and/or environment information/data from a patient record (e.g., electronic health record and/or other patient record) stored in a patient record database by the index information/data computing entity 30.

In an example embodiment, an index information/data computing entity 30 may receive the patient information/data and/or environment information/data corresponding to a patient (e.g., associated with a patient identifier). The index information/data computing entity 30 may identify a patient record from a patient record database stored by the index information/data computing entity 30 based on the patient identifier associated with the patient information/data and/or environment information/data and update the patient record based on the patient information/data and/or environment information/data. In an example embodiment, the patient record is an electronic health record. In an example embodiment, the patient record is a patient record corresponding to a particular healthcare interaction (e.g., hospital visit, intensive care unit (ICU) stay, and/or the like). For example, the patient record may be used to identify one or more interventions for the patient, determine the efficacy of one or more interventions, and/or the like. In various embodiments, the index information/data computing entity 30 is configured to receive requests for information/data stored in one or more patient records (e.g., provided by one or more user computing entities 20) and provide the requested information/data (e.g., when the requestor has the appropriate credentials for accessing the requested information/data).

Continuing to block 608, it is determined, based on the patient information/data and/or environment information/data, if a trigger event has occurred. For example, the analysis computing entity may determine, based on the patient information/data and/or environment information/data, whether a trigger event has occurred. In various embodiments, a trigger event may be a determination that a patient is experiencing delirium to a confidence level that meets or surpasses threshold confidence level. For example, it may be determined that a patient is experiencing delirium based on movement of the patient (e.g., movement of the patient's wrist determined based on movement information/data corresponding to a patient, movement of the patients head as determined by changes in position of the patient's head between various determinations of the patient's head position), facial AUs of the patient information/data corresponding to the patient, facial expressions of the patient information/data corresponding to the patient, and/or the like, it may be determined that the patient is experiencing delirium with a given confidence level. For example, a delirium model may receive as inputs various elements of the patient information/data (e.g., wrist movement, facial AUs, facial expressions, and/or the like) and provide a likelihood and/or probability that the patient is experiencing delirium. When the likelihood and/or probability that the patient is experiencing delirium that meets or is greater than a threshold confidence level threshold, it may be determined that the patient is experiencing delirium and it may be determined that a trigger event has occurred.

In another example, as shown in FIG. 6A, patients experiencing different levels of pain may exhibit different levels of activity. Similarly, patients experiencing different levels of pain may exhibit different facial expressions, different body postures, and/or the like. Additionally, when a patient's pain level changes, the patient's activity level, distribution of facial features, distribution of body postures, and/or the like may also change. Various embodiments of the present invention may be configured to determine a patient pain level and/or change in patient pain level and issue an alert accordingly. For example, a patient's activity level, body posture, facial expressions, facial AUs, and/or the like may be monitored to determine a pain level being experienced by the patient. If the pain level is greater than a threshold pain level, it may be determined that a trigger event has occurred. In another example, a patient's activity level, body posture, facial expressions, facial AUs, and/or the like may be monitored to determine a change in a patient's pain level (e.g., based on changes in the patient's activity level, body posture, facial expressions, facial AUs, and/or the like).

When it is determined that the patient's pain level has changed (increased and/or decreased) by at least a threshold pain level change, it may be determined that a trigger event has occurred, in an example embodiment.

In various embodiments, a variety of trigger events may be defined. For example, one or more trigger events may be defined corresponding to a worsening of a patient's condition. In another example, one or more trigger events may be defined corresponding to an improvement of a patient's condition. In various embodiments, a trigger event may be defined corresponding to a change in a patient's pain level, activity level, and/or the like. In an example embodiment, a trigger event may correspond to the environment about the patient. For example, if the light level, noise level, or visitation frequency is above or below a corresponding threshold level, it may be determined that a trigger event has occurred. In an example embodiment, the threshold level corresponding to a light level, noise level, or visitation frequency may be time of day and/or patient condition dependent. For example, the light level, noise level, and visitation frequency threshold level during the night hours may be lower (e.g., such that the patient's room is darker, quieter, and has fewer visits) compared to during the daytime hours. In another example, the light level, noise level, and visitation frequency threshold level may be different for a patient determined to be experiencing delirium compared to a patient not experiencing delirium.

When it is determined at block 608 that a trigger event has not occurred, the system returns to block 602 to receive and process sensor information/data. When it is determined at block 608 that a trigger event has occurred, the process may continue to block 610.

At block 610, an intervention for the patient may be determined. For example, the analysis computing entity 10 may optionally determine an intervention for the patient. In various embodiments, the intervention is determined based on the trigger event, the patient and/or environment information/data used to determine that the trigger event occurred, and/or information/data from the patient record. For example, if the trigger event is that the patient is being visited too frequently during the night hours, the intervention may be to adjust the visitation schedule for the patient. Similarly, if the trigger event corresponds to a light level or noise level within the patient's room, the intervention may correspond to appropriately adjusting the light and/or noise within the patient's room. In another example, if the trigger event corresponds to patient's conditioning worsening, the intervention may be a treatment (e.g., chemical treatment/prescription, procedure, and/or the like) that is commonly provided to a patient with the patient's condition.

At block 612, an alert is provided. In an example embodiment, the determined intervention is provided with the alert. For example, the analysis computing entity 10 may provide an alert such that the alert is received by a user computing entity 20. For example, the alert may indicate the patient identifier (and/or patient name, patient room number, and/or the like), the trigger event that triggered the alert, (optionally) a suggested intervention, and/or the like. In various embodiments, a user computing entity 20 may receive an alert, and responsive thereto, provide a user-perceivable notification (e.g., visual, haptic, audible, and/or the like) of the receipt of the alert. For example, the user computing entity 20 may be configured to provide at least a portion of the alert via an interactive user interface. For example, the user computing entity 20 may be configured to display the patient identifier (and/or patient name, patient room number, and/or the like), the trigger event that triggered the alert, (optionally) a suggested intervention and/or the like via an interactive user interface. The user (e.g., a care provider) may then take action based on the received alert. For example, the user may perform the suggested intervention and/or determine and perform another intervention.

Determining and Providing Facial Expression Information/Data

In various embodiments, one or more images of a sequence of images of the patient and/or environment about the patient may be analyzed to determine facial expression information/data for the patient. For example, one or more faces may be detected (e.g. using the face detection computer program code) in the one or more images and at least one of the detected faces may be determined and/or identified to be the face of the patient (e.g., using the face recognition computer program code). The face of the patient in the one or more images may then be analyzed to determine facial expression information/data. In various embodiments, the facial expression information/data may be determined via analysis of the face of the patient in the one or more images via a train neural network. For example, a multi-stage convolutional neural network (CNN) may be used to align the face of a patient in one or more images. Features of the face of the patient may then be extracted, normalized, and stored as feature embeddings via a trained neural network. The feature embeddings may then be provided as input for a k-nearest neighbor classifier to identify the facial expression made by the user in the one or more images.

FIG. 7 provides a flowchart illustrating various processes, procedures, operations, and/or the like for determining facial expression information/data corresponding to a patient and providing the facial expression information/data. Starting at block 702, sequence(s) of images of the patient and/or environment about the patient are received. For example, the analysis computing entity 10 may receive (e.g., via communication interface 120) sequence(s) of images of the patient and/or environment about the patient. For example, visual sensor(s) 50 may capture sequence(s) of images of the patient and/or environment about the patient. In an example embodiment, a patient identifier and/or sensor identifier is received with the sensor information/data. For example, the visual sensor(s) 50 may provide a patient identifier and/or sensor identifier along with the sequence(s) of images of the patient and/or environment about the patient. In an example embodiment, the sensor identifier corresponds to a known location (e.g., a particular patient room number) and may be used to identify the patient (e.g., based on a patient assigned to the particular patient room number).

At block 704, the patient's face is identified and aligned based on an analyzed image of the sequence of images. For example, the analysis computing entity 10 may identify the patient's face in an analyzed image of the sequence of images and align the identified patient's face to a predetermined alignment, orientation and/or the like. For example, the analysis computing entity 10 may operate and/or execute a multi-stage CNN configured to identify the patient's face in the analyzed image (e.g., possibly using on the face detection and/or face recognition computer program code) and/or to align the identified face of the patient. For example, the portion of an analyzed image corresponding to the face of the patient may be modified such that the face of the patient is provided in a predetermined alignment, orientation, and/or the like. For example, the portion of an analyzed image may be modified to generate an aligned face image comprising the face of the patient in a predetermined alignment, orientation, and/or the like.

At block 706, facial features are extracted from an aligned face image. For example, the analysis computing entity 10 may extract facial features from an aligned face image. In an example embodiment, the facial features are extracted form an aligned face image using a neural network, such as a pre-trained Inception-Resnet-V1 model, in an example embodiment.

At block 708, the extracted facial features are normalized. For example, the analysis computing entity 10 may normalize the extracted facial features. For example, the extracted facial features may be normalized using an L2 normalization and/or another normalization.

At block 710, the normalized extracted facial features are stored as feature embeddings. For example, the analysis computing entity 10 may store (e.g., in memory 110, 115) the normalized extracted facial features as feature embeddings. In an example embodiment, blocks 706-710 are performed by a (pre-trained) faceNet network, model, and/or the like.

At block 712, a facial expression for the face of the patient in the analyzed image is determined based on the corresponding feature embeddings. For example, the analysis computing entity 10 may determine a facial expression for the face of the patient in the analyzed image based on the corresponding feature embeddings. For example, the stored feature embeddings corresponding to the patient's face in an analyzed image may be analyzed to identify a facial expression for the face of the patient in the analyzed image. In an example embodiment, the facial expression for the face of the patient is determined based on providing the feature embeddings as input to a k-nearest neighbor (KNN) classifier. For example, the facial expression of the patient may be determined by a KNN classifier based on the feature embeddings.

At block 714, the facial expression and/or an indication thereof (e.g., a facial expression identifier) is provided. For example, the analysis computing entity 10 may provide (e.g., via communications interface 120) facial expression and/or indication thereof. For example, the analysis computing entity 10 may provide facial expression and/or indication thereof such that the facial expression and/or indication thereof is received by a user computing entity 20, index information/data computing entity 30, and/or in-room display 70. In various embodiments, the facial expression and/or indication thereof may be provided in association with a patient identifier. In an example embodiment, the facial expression and/or indication thereof may be provided with the analyzed image and/or a portion thereof (e.g., the portion of the analyzed image comprising the face of the patient).

For example, facial expression and/or indication thereof (e.g., and possibly the corresponding patient identifier and/or analyzed image and/or portion thereof) may be received by an in-room display 70 corresponding to a patient identifier corresponding to the sensor information/data and/or a location identifier corresponding to one or more sensor identifiers corresponding to the sequence of images from which the analyzed image originated. The in-room display 70 may process the received facial expression and/or indication thereof and provide (e.g., display) facial expression and/or indication thereof and/or the analyzed image and/or portion thereof. For example, the in-room display 70 may provide an interactive user interface that a care provider may use to view patient information/data (e.g., facial expression information/data) and/or environment information/data corresponding to the patient located within the same patient room 1 as the in-room display 70.

For example, facial expression and/or indication thereof may be received by a user computing entity 20 (possibly as part of patient information/data and/or environment information/data) corresponding to a care provider or other user associated with the patient (e.g., assigned to the patient and/or the like). In an example embodiment, the user computing entity 20 may provide an interactive user interface through which a user may access patient information/data and/or environment information/data corresponding to a patient. In an example embodiment, the user may interact with the interactive user interface to view the patient information/data (e.g., facial expression and/or indication thereof) and/or environment information/data for a patient. In an example embodiment, the user computing entity 20 may access patient information/data and/or environment information/data from a patient record (e.g., electronic health record and/or other patient record) stored in a patient record database by the index information/data computing entity 30.

In an example embodiment, an index information/data computing entity 30 may receive the facial expression and/or indication thereof corresponding to a patient (e.g., associated with a patient identifier). The index information/data computing entity 30 may identify a patient record from a patient record database stored by the index information/data computing entity 30 based on the patient identifier associated with the facial expression and/or indication thereof and update the patient record based on the facial expression and/or indication thereof. In an example embodiment, the patient record is an electronic health record. In an example embodiment, the patient record is a patient record corresponding to a particular healthcare interaction (e.g., hospital visit, intensive care unit (ICU) stay, and/or the like). For example, the patient record may be used to identify one or more interventions for the patient, determine the efficacy of one or more interventions, and/or the like. In various embodiments, the index information/data computing entity 30 is configured to receive requests for information/data stored in one or more patient records (e.g., provided by one or more user computing entities 20) and provide the requested information/data (e.g., when the requestor has the appropriate credentials for accessing the requested information/data).

In an example embodiment, the facial expression and/or indication thereof may be provided as input to another process running and/or executing on the analysis computing entity 10 to determine a patient's pain level, determine if the patient is experiencing delirium, and/or the like. For example, FIG. 7A shows the distribution of facial action units for patients experiencing pain (according to a nurse survey) versus patients not experiencing pain (according to the nurse survey).

Determining and Providing Body Posture Information/Data

In various embodiments, one or more images of a sequence of images of the patient and/or environment about the patient may be analyzed to determine body position information/data for the patient. For example, one or more faces may be detected (e.g. using the face detection computer program code) in the one or more images and at least one of the detected faces may be determined and/or identified to be the face of the patient (e.g., using the face recognition computer program code). The body associated with the face of the patient in the one or more images may then be analyzed to determine a body posture of the patient. In various embodiments, the body position information/data may be determined via analysis of the joints and limbs of the patient in the one or more images via a train neural network.

For example, a neural network may be used to identify one or more limbs and joints of a patient in one or more images. Positions of the limbs and joints may be separately determined (e.g., via one or more two branch stages of a CNN) and then combined to refine the determination of the positions of the limbs and the joints of the patient. Once the positions of the limbs and joints of the patient are determined with a sufficient level of confidence, features may be extracted from the image (e.g., features corresponding to the patient's limbs and joints) and the features may be analyzed to classify a body posture for the patient (e.g., using a KNN classifier).

FIG. 8 provides a flowchart illustrating various processes, procedures, operations, and/or the like for determining body position information/data corresponding to a patient and providing the body position information/data. Starting at block 802, sequence(s) of images of the patient and/or environment about the patient are received. For example, the analysis computing entity 10 may receive (e.g., via communication interface 120) sequence(s) of images of the patient and/or environment about the patient. For example, visual sensor(s) 50 may capture sequence(s) of images of the patient and/or environment about the patient. In an example embodiment, a patient identifier and/or sensor identifier is received with the sensor information/data. For example, the visual sensor(s) 50 may provide a patient identifier and/or sensor identifier along with the sequence(s) of images of the patient and/or environment about the patient. In an example embodiment, the sensor identifier corresponds to a known location (e.g., a particular patient room number) and may be used to identify the patient (e.g., based on a patient assigned to the particular patient room number).

At block 804, various pre-processing procedures may be performed. For example, the analysis computing entity 10 may identify the patient's face in an analyzed image of the sequence of images. For example, the analysis computing entity 10 may operate and/or execute a neural network to perform one or more pre-processing steps. In an example embodiment, the pone or more pre-processing steps may include providing the analyzed image to a visual group geometry (VGG) or similar trained image classification model. In an example embodiment, the pre-processing steps may include analyzing the analyzed image using the first ten stages of a VGG-19 network. For example, the portion of an analyzed image corresponding to the face of the patient may be modified such that the face of the patient is provided in a predetermined alignment, orientation, and/or the like. For example, the portion of an analyzed image may be modified to generate an aligned face image comprising the face of the patient in a predetermined alignment, orientation, and/or the like.

In various embodiments, the output of the pre-processing of the analyzed image is provided to a multi-stage, two branch CNN. For example, the image of the face of the patient in the predetermined alignment, orientation, and/or the like, may be provided to the multi-stage, two branch CNN. In an example embodiment, one of the branches of each stage predicts joint confidence maps for various joints of the patient's body and the other branch predicts the limb part affinity fields for the limbs of the patient's body. After each stage, the predicted joint confidence map for the patient's body and prediction of the limb part affinity field for the patient's body are combined to determine a level of consistency between two predictions. The predictions of the joint confidence maps and limb part affinity fields of the patient's body are then refined in the stage based on the level of consistency between the two predictions, the other prediction, and/or the like. In an example embodiment, the multi-stage, two branch CNN has three stages.

For example, at block 806, joint confidence maps are determined based on the pre-processed analyzed image. For example, an analysis computing entity 10 may determine joint confidence maps for various joints of the patient's body based on the pre-processed analyzed image. For example, a branch of a stage of a CNN may be used to predict joint confidence maps for various joints of the patient's body based on the pre-processed analyzed image. For example, at block 808, limb part affinity fields are determined based on the pre-processed analyzed image. For example, an analysis computing entity 10 may determine limb part affinity fields for various limbs of the patient's body based on the pre-processed analyzed image. For example, a branch of a stage of a CNN may be used to predict limb part affinity fields for various limbs of the patient's body based on the pre-processed analyzed image. At block 810, the predicted joint confidence maps and the predicted limb part affinity fields may be combined. For example, the analysis computing entity 10 may combine the predicted joint confidence maps and the predicted limb part affinity fields. For example, feedback regarding the consistency of the joint confidence maps and the predicted limb part affinity fields may be determined, generated, and/or the like. At block 812, the predicted joint confidence maps and the predicted limb part affinity fields may be refined. For example, based on the feedback determined, generated, and/or the like at block 810, the predicted joint confidence maps and the predicted limb part affinity fields may be refined. For example, the analysis computing entity 10 may refine the predicted joint confidence maps and the predicted limb part affinity fields based on the feedback determined, generated, and/or the like at block 810. The combination and refinement process may be repeated one or more times. For example, two, three, or more stages may be used to determine the refined joint confidence maps and refined limb part affinity fields. For example, the analysis computing entity 10 may operated and/or execute a three stage (with two branches at each stage) CNN to determine refined joint confidence maps and the refined limb part affinity fields.

At block 814, the features are extracted from the refined joint confidence maps and/or refined limb part affinity fields. For example, the analysis computing entity 10 may extract features from the refined joint confidence maps and/or refined limb part affinity fields. For example, the length and angles of one or more limbs of the patient's body may be extracted from the refined limb part affinity fields. Any missing values may be imputed using KNN imputation. For example, KNN imputation may be used to replace any missing values in the set of extracted features (e.g., length and angles of one or more limbs) with a plausible values.

At block 816, a classification of the patient's body posture is determined based on the extracted features. For example, the analysis computing entity 10 may analyze the extracted features to determine a classification of the patient's body posture. In an example embodiment, a pre-trained KNN classifier is used to determine a classification for the patient's body posture based on the extracted features. For example, the patient's body position in the analyzed image may be determined.

At block 818, the body position and/or an indication thereof (e.g., a body position identifier) is provided. For example, the analysis computing entity 10 may provide (e.g., via communications interface 120) a body position and/or indication thereof corresponding to the patient. For example, the analysis computing entity 10 may provide body position and/or indication thereof for the patient such that the patient body position and/or indication thereof is received by a user computing entity 20, index information/data computing entity 30, and/or in-room display 70. In various embodiments, the patient body position and/or indication thereof may be provided in association with a patient identifier. In an example embodiment, the patient body position and/or indication thereof may be provided with the analyzed image and/or a portion thereof (e.g., the portion of the analyzed image comprising the body of the patient).

For example, patient body position and/or an indication thereof (e.g., and possibly the corresponding patient identifier and/or analyzed image and/or portion thereof) may be received by an in-room display 70 corresponding to a patient identifier corresponding to the sensor information/data and/or a location identifier corresponding to one or more sensor identifiers corresponding to the sequence of images from which the analyzed image originated. The in-room display 70 may process the received patient body position and/or indication thereof and provide (e.g., display) facial expression and/or indication thereof and/or the analyzed image and/or portion thereof. For example, the in-room display 70 may provide an interactive user interface that a care provider may use to view patient information/data (e.g., facial expression information/data) and/or environment information/data corresponding to the patient located within the same patient room 1 as the in-room display 70.

For example, the patient body position and/or an indication thereof may be received by a user computing entity 20 (possibly as part of patient information/data and/or environment information/data) corresponding to a care provider or other user associated with the patient (e.g., assigned to the patient and/or the like). In an example embodiment, the user computing entity 20 may provide an interactive user interface through which a user may access patient information/data and/or environment information/data corresponding to a patient. In an example embodiment, the user may interact with the interactive user interface to view the patient information/data (e.g., patient body position and/or indication thereof) and/or environment information/data for a patient. In an example embodiment, the user computing entity 20 may access patient information/data and/or environment information/data from a patient record (e.g., electronic health record and/or other patient record) stored in a patient record database by the index information/data computing entity 30.

In an example embodiment, an index information/data computing entity 30 may receive the body position and/or indication thereof corresponding to a patient (e.g., associated with a patient identifier). The index information/data computing entity 30 may identify a patient record from a patient record database stored by the index information/data computing entity 30 based on the patient identifier associated with the body position and/or indication thereof and update the patient record based on the body position and/or indication thereof. In an example embodiment, the patient record is an electronic health record. In an example embodiment, the patient record is a patient record corresponding to a particular healthcare interaction (e.g., hospital visit, intensive care unit (ICU) stay, and/or the like). For example, the patient record may be used to identify one or more interventions for the patient, determine the efficacy of one or more interventions, and/or the like. In various embodiments, the index information/data computing entity 30 is configured to receive requests for information/data stored in one or more patient records (e.g., provided by one or more user computing entities 20) and provide the requested information/data (e.g., when the requestor has the appropriate credentials for accessing the requested information/data).

In an example embodiment, the patient body position and/or indication thereof may be provided as input to another process running and/or executing on the analysis computing entity 10 to determine a patient's pain level, determine if the patient is experiencing delirium, and/or the like. For example, FIG. 8A shows the distribution of body postures for patients experiencing pain (according to a nurse survey) versus patients not experiencing pain (according to the nurse survey).

Technical Advantages

Various embodiments of the present invention provide technical advantages over traditional patient monitoring systems. For example, various embodiments of the present invention provide for pervasive monitoring of a patient and the environment about the patient. The patient information/data and/or environment information/data generated through the pervasive monitoring of the patient and the environment about the patient may be used to update a patient record and may be used as input to an analysis and/or evaluation of the patient's condition, changes in the patient's condition, predictions regarding a future condition of the patient, determine suggested interventions (e.g., treatments, changes to the patient's care plan, an adjustment of the light or noise level within the patient's room, and/or the like). Additionally, the pervasive monitoring of the patient provides an objective determination of various aspects of the patient's condition. For example, the pervasive monitoring and analysis and/or evaluation of the patient information/data generated thereby may be used to determine an objective measure of the patient's pain level. Traditional monitoring systems may monitor physiological measurements of the patient, but fail to incorporate the physiological measurements into an analysis of the patient that provides improved insight to care providers. Thus, various embodiments of the present invention provide an improvement over traditional patient monitoring systems.

IV. Conclusion

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A patient monitoring system, the system comprising:
   a plurality of sensors, the plurality of sensors comprising:
      at least one visual sensor configured to capture images of a patient and provide the images of the patient such that an analysis computing entity receives the images of the patient, and
      at least one wearable sensor, the at least one wearable sensor configured to (1) capture wearable data, the wearable data comprising at least one of (a) biometric data of the patient or (b) movement data of the patient, and (2) provide the wearable data such that the analysis computing entity receives the wearable data; and the analysis computing entity, comprising a processor, a memory storing computer program code, and a communications interface, the memory and computer program code, with the processor, configured to cause the analysis computing entity to at least:
receive the images of the patient and the wearable data, analyze at least one of the images of the patient and the wearable data to determine objective patient data, wherein the objective patient data comprises a body posture of the patient determined by analyzing the at least one of the images of the patient, and
update a patient record based at least in part on the objective patient data,
wherein to determine the body posture of the patient, the memory and computer program code, with the processor, are further configured to cause the analysis computing entity to at least:
predict joint confidence maps for various joints of the patient's body based at least in part on the image;
predict limb part affinity fields for various limbs of the patient's body based at least in part on the image;
combine the predicted joint confidence maps and predicted limb part affinity fields;
refine the predicted joint confidence maps and predicted limb part affinity fields based at least in part on the combination thereof;
extract limb features based at least in part on the refined limb part affinity fields; and
analyze the extracted limb features using a classifier neural network to determine a body position of the patient.

2. The system of claim 1, wherein the plurality of sensors comprise one or more sensors configured to capture environment data and provide the environment data such that the analysis computing entity receives the environment data.

3. The system of claim 2, wherein at least a portion of the environment data is captured by the at least one visual sensor.

4. The system of claim 2, wherein the environment data comprises information regarding at least one of ambient light within a patient room, ambient sound within the patient room, or the presence of other individuals in the patient room.

5. The system of claim 2, wherein the objective patient data comprises at least a portion of the environment data or the result of an analysis of the environment data.

6. The system of claim 1, wherein analyzing at least one of the images of the patient comprises at least one of identifying a facial expression of the patient or identifying a head position of the patient.

7. The system of claim 1, wherein the analysis computing entity is configured to analyze at least one of the images of the patient via a trained convolutional neural network.

8. The system of claim 1, wherein the analysis computing entity is configured to, based at least in part on the analysis of the at least one of the images of the patient and the wearable data to determine whether the patient is delirious or not.

9. The system of claim 8, wherein the determination of whether or not a patient is delirious is based at least in part on at least one of patient facial expression determined via analysis of the at least one of the images of the patient, patient head position determined via analysis of the at least one of the images of the patient, or patient wrist movement determined via analysis of the wearable data.

10. The system of claim 1, wherein the analysis computing entity is configured to determine, based at least in part on the objective patient data, whether a trigger event has occurred and, responsive to determining that a trigger event has occurred, providing an alert such that a user computing entity receives the alert and causes a user-perceivable notification of the alert to be provided via a user interface thereof.

11. The system of claim 10, wherein the analysis computing entity is configured to receive a care plan update provided by the user computing entity and update the patient record based at least in part on the care plan update.

12. The system of claim 10, wherein the analysis computing entity is configured to identify an intervention based at least in part on the trigger event and the alert identifies the identified intervention.

13. The system of claim 1, wherein the patient record is an electronic health record.

14. The system of claim 1, wherein the at least one wearable sensor comprises an accelerometer.

15. A method for notifying a care provider about a condition of a patient, the method comprising:
receiving, by an analysis computing entity, sensor data corresponding to a patient, the sensor data captured by a plurality of sensors located in the proximity of the patient, the sensor data comprising a sequence of images of the patient and wearable data captured by a wearable sensor worn by the patient;
analyzing, by the analysis computing entity, at least one of (1) the sequence of images of the patient to determine at least one of (a) changes to head position of the patient or (b) facial expressions of the patient or (2) the wearable data to determine patient movement data for the patient;
analyzing, by the analysis computing entity, at least one of the sequence of images of the patient to determine a body posture of the patient;
based at least in part on at least one of the (1) changes in head position of the patient or facial expressions of the patient, (2) wrist movement data for the patient, or (3) the body posture of the patient, determining, by the analysis computing entity, whether a trigger event has occurred; and
when it is determined that a trigger event has occurred, generating and providing an alert indicating that the trigger event has occurred such that a user computing entity receives the alert, the user computing entity configured to provide a user-perceivable notification of the alert via a user interface thereof,
wherein determining the body posture of the patient comprises:
predicting joint confidence maps for various joints of the patient's body based at least in part on the image;
predicting limb part affinity fields for various limbs of the patient's body based at least in part on the image;
combining the predicted joint confidence maps and predicted limb part affinity fields;
refining the predicted joint confidence maps and predicted limb part affinity fields based at least in part on the combination thereof;
extracting limb features based at least in part on the refined limb part affinity fields; and
analyzing the extracted limb features using a classifier neural network to determine a body position of the patient.

16. The method of claim 15, wherein analyzing an image of the sequence of images of the patient to determine a facial expression of the patient comprises:

extracting facial features from a portion of the image corresponding to the patient's face; and analyzing the extracted facial features using a classifier neural network to determine a facial expression of the patient.

17. The method of claim 15, wherein the movement data corresponds to movement of the patient's wrist and the trigger event is determining that the patient is experiencing delirium.

18. The method of claim 15, further comprising receiving environment data captured by at least some of the plurality of sensors in the proximity of the patient, wherein the determination of whether the trigger event has occurred is based at least in part on the environment data.

* * * * *